(12) United States Patent
Xiang et al.

(10) Patent No.: US 12,364,449 B2
(45) Date of Patent: Jul. 22, 2025

(54) IMAGING SYSTEMS AND METHODS

(71) Applicant: SHANGHAI UNITED IMAGING HEALTHCARE CO., LTD., Shanghai (CN)

(72) Inventors: Jun Xiang, Shanghai (CN); Juan Feng, Shanghai (CN); Weiyi Wang, Shanghai (CN); Yu Zhang, Shanghai (CN); Hanyu Wang, Shanghai (CN); Jie Niu, Shanghai (CN); Hui Yin, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 391 days.

(21) Appl. No.: 17/809,555

(22) Filed: Jun. 28, 2022

(65) Prior Publication Data

US 2022/0323027 A1 Oct. 13, 2022

Related U.S. Application Data

(63) Continuation of application No. PCT/CN2020/139506, filed on Dec. 25, 2020.

(30) Foreign Application Priority Data

Dec. 28, 2019 (CN) .......................... 201911386706.5
Dec. 31, 2019 (CN) .......................... 201911403876.X
Mar. 16, 2020 (CN) .......................... 202010184286.9

(51) Int. Cl.
*A61B 6/00* (2024.01)
*A61B 6/02* (2006.01)
(Continued)

(52) U.S. Cl.
CPC ............ *A61B 6/4007* (2013.01); *A61B 6/025* (2013.01); *A61B 6/0414* (2013.01); *A61B 6/107* (2013.01);
(Continued)

(58) Field of Classification Search
CPC ..... A61B 6/032; A61B 6/4014; A61B 6/4007; A61B 6/4021; A61B 6/405; A61B 6/4064; H05G 1/00; H05G 1/04
See application file for complete search history.

(56) References Cited

U.S. PATENT DOCUMENTS

2006/0002506 A1 1/2006 Pelc
2007/0025509 A1 2/2007 Pang et al.
(Continued)

FOREIGN PATENT DOCUMENTS

CN 104095643 A 10/2014
CN 104323787 2/2015
(Continued)

OTHER PUBLICATIONS

International Search Report in PCT/CN2020/139506 mailed on Mar. 24, 2021, 6 pages.
(Continued)

*Primary Examiner* — Don K Wong
(74) *Attorney, Agent, or Firm* — METIS IP LLC

(57) ABSTRACT

The present disclosure is related to an imaging system. The imaging system may include at least one array radiation source and a detector. Each of the at least one array radiation source may include a plurality of point radiation sources. The at least one array radiation source may be configured to emit at least one radiation beam. The detector may be configured to detect at least part of the at least one radiation beam.

20 Claims, 16 Drawing Sheets

(51) Int. Cl.
  *A61B 6/04*    (2006.01)
  *A61B 6/10*    (2006.01)
  *A61B 6/40*    (2024.01)
  *A61B 6/42*    (2024.01)
  *A61B 6/50*    (2024.01)
  *A61B 6/58*    (2024.01)

(52) U.S. Cl.
  CPC .......... *A61B 6/4035* (2013.01); *A61B 6/4241* (2013.01); *A61B 6/502* (2013.01); *A61B 6/542* (2013.01); *A61B 6/588* (2013.01)

(56) References Cited

U.S. PATENT DOCUMENTS

| | | |
|---|---|---|
| 2009/0262891 A1 | 10/2009 | Zhang et al. |
| 2010/0034450 A1 | 2/2010 | Mertelmeier |
| 2010/0246759 A1 | 9/2010 | Ogura et al. |
| 2010/0284509 A1 | 11/2010 | Oreper |
| 2011/0002439 A1 | 1/2011 | Zhang |
| 2011/0235774 A1 | 9/2011 | Dolazza et al. |
| 2011/0280367 A1 | 11/2011 | Baeumer et al. |
| 2012/0134465 A1 | 5/2012 | Lee et al. |
| 2012/0163531 A1 | 6/2012 | Zhang et al. |
| 2012/0195403 A1 | 8/2012 | Vedantham et al. |
| 2013/0163718 A1 | 6/2013 | Lindenberg et al. |
| 2013/0301799 A1 | 11/2013 | Kang et al. |
| 2015/0150524 A1 | 6/2015 | Yorkston et al. |
| 2015/0282774 A1 | 10/2015 | Lee et al. |
| 2015/0335306 A1 | 11/2015 | Do et al. |
| 2015/0359504 A1 | 12/2015 | Zhou et al. |
| 2016/0106382 A1 | 4/2016 | Lu et al. |
| 2016/0235382 A1* | 8/2016 | Besson .................. A61B 6/032 |
| 2016/0310087 A1 | 10/2016 | Myrman |
| 2017/0027531 A1 | 2/2017 | Shiozawa et al. |
| 2017/0265822 A1 | 9/2017 | Du |
| 2019/0056338 A1 | 2/2019 | Li et al. |
| 2019/0209107 A1 | 7/2019 | Vogtmeier et al. |

FOREIGN PATENT DOCUMENTS

| | | |
|---|---|---|
| CN | 104434165 A | 3/2015 |
| CN | 209172280 | 7/2019 |
| CN | 111358478 | 7/2020 |
| DE | 19812995 A1 | 10/1999 |
| DE | 102010011662 A1 | 9/2011 |
| DE | 102010011663 A1 | 9/2011 |
| DE | 102010062541 A1 | 6/2012 |
| EP | 0747008 A1 | 12/1996 |
| EP | 2819145 A1 | 12/2014 |
| EP | 3062093 A1 | 8/2016 |
| EP | 3586752 A1 | 1/2020 |
| JP | H0638957 A | 2/1994 |
| WO | 2007038306 A2 | 4/2007 |
| WO | 2014080552 A1 | 5/2014 |

OTHER PUBLICATIONS

Written Opinion in PCT/CN2020/139506 mailed on Mar. 24, 2021, 6 pages.

He, Peng et al., Experimental Study of Material K-Edge Characteristics Identification Based on X-ray Photon-Counting Detection Technique, Spectroscopy and Spectral Analysis, 38(12): 3929-3933, 2018.

Chi, Zhijun, Research on advanced X-ray imaging methods based on Thomson scattering X-ray source(Part One), Basic science series of full-text database of doctoral dissertations in China, 2017, 70 pages.

Chi, Zhijun, Research on advanced X-ray imaging methods based on Thomson scattering X-ray source(Part Two), Basic science series of full-text database of doctoral dissertations in China, 2017, 68 pages.

The Partial Supplementary European Search Report in European Application No. 20906569.7 mailed on Jan. 2, 2023, 11 pages.

* cited by examiner

1500

```
┌─────────────────────────────────────────────────┐
│ Causing each point radiation source of a        │
│ plurality of point radiation sources of an      │
│ array radiation source to simultaneously emit   │ 1510
│ a radiation beam to a subject, each radiation   │
│ beam including a plurality of X-ray photons,    │
│ wherein the subject is located between the      │
│ array radiation source and a detector, and at   │
│ least two radiation beams emitted by the        │
│ plurality of point radiation sources are        │
│ different                                       │
└─────────────────────────────────────────────────┘
                         │
                         ▼
┌─────────────────────────────────────────────────┐
│ For each of the plurality of point radiation    │
│ sources, obtaining, by the detector, energies   │
│ of detected X-ray photons corresponding to the  │ 1520
│ radiation beam emitted by the each point        │
│ radiation source and a count of the detected    │
│ X-ray photons corresponding to the radiation    │
│ beam                                            │
└─────────────────────────────────────────────────┘
                         │
                         ▼
┌─────────────────────────────────────────────────┐
│ For each of the plurality of point radiation    │
│ sources, determining a candidate image          │
│ corresponding to the each point radiation       │
│ source based on an energy range of the          │ 1530
│ radiation beam emitted by the each point        │
│ radiation source, the energies of the detected  │
│ X-ray photons corresponding to the radiation    │
│ beam, and the count of detected X-ray photons   │
│ corresponding to the radiation beam             │
└─────────────────────────────────────────────────┘
                         │
                         ▼
┌─────────────────────────────────────────────────┐
│ Generating a target image based on the          │ 1540
│ candidate images corresponding to the           │
│ plurality of point radiation sources            │
└─────────────────────────────────────────────────┘
```

FIG. 15

IMAGING SYSTEMS AND METHODS

CROSS-REFERENCE TO RELATED APPLICATIONS

This application is a Continuation of International Application No. PCT/CN2020/139506, filed on Dec. 25, 2020, which claims priority of Chinese Patent Application No. 202010184286.9, filed on Mar. 16, 2020, Chinese Patent Application No. 201911403876.X, filed on Dec. 31, 2019, and Chinese Patent Application No. 201911386706.5, filed on Dec. 28, 2019, the contents of each of which are hereby incorporated by reference.

TECHNICAL FIELD

This disclosure generally relates to imaging systems and methods, and more particularly, relates to an array radiation source in a medical device.

BACKGROUND

Medical imaging techniques have been widely used in clinical examinations and medical diagnoses in recent years. For example, with the development of X-ray imaging technology, a digital breast tomosynthesis (DBT) system has become more and more common in breast disease diagnosis. A high-quality medical image obtained by the DBT system can provide sufficient and effective information for the breast disease diagnosis. Therefore, it is desirable to provide effective imaging systems and methods to improve the quality of an image.

SUMMARY

According to an aspect of the present disclosure, an imaging system may be provided. The imaging system may include at least one array radiation source and a detector. Each of the at least one array radiation source may include a plurality of point radiation sources. The at least one array radiation source may be configured to emit at least one radiation beam. The detector may be configured to detect at least part of the at least one radiation beam.

In some embodiments, the at least one array radiation source may include a planar array radiation source. The planar array radiation source may include at least one radiation source panel. The plurality of point radiation sources may be configured on the at least one radiation source panel.

In some embodiments, the planar array radiation source may include two radiation source panels arranged at an angle.

In some embodiments, the angle between the two radiation source panels may be adjustable.

In some embodiments, a range of the angle between the two radiation source panels may be from 140° to 180°.

In some embodiments, the imaging system may include a control device configured to control the at least one array radiation source to move along a guide rail to adjust a distance between the at least one array radiation source and the detector.

In some embodiments, the imaging system may include a control device configured to adjust at least one parameter of the at least one array radiation source.

In some embodiments, the at least one parameter of the at least one array radiation source may include at least one of a position of the at least one array radiation source, a position of at least one of the plurality of point radiation sources, an orientation of the at least one of the plurality of point radiation sources, or a radiation dose of the at least one radiation beam.

In some embodiments, at least two radiation beams emitted by the array radiation sources may be of different energy ranges.

In some embodiments, a plurality of energy ranges of a plurality of radiation beams emitted by the array radiation sources may not overlap, and an energy difference between consecutive energy ranges may be not less than an energy resolution of the detector.

In some embodiments, at least one of the plurality of point radiation sources may include at least one of a high voltage generator, a tube, a filtering device, or a control device. The high voltage generator may be configured to generate a high-voltage for a tube. The tube may be configured to generate the radiation beam based on the high-voltage. The filtering device may be configured to absorb a radiation beam lower than a preset energy range. The control device may be configured to control the high-voltage generated by the high voltage generator or the energy range of the radiation beam generated by the tube.

In some embodiments, the point radiation source may include at least one of a cold cathode ray source or a hot cathode ray source.

In some embodiments, the point radiation source may include an electromagnetic coil configured to control a moving direction of the radiation beam.

In some embodiments, the point radiation source may be a monochromatic radiation source.

In some embodiments, each of the at least one radiation beam may include a plurality of X-ray photons. The detector may be configured to detect an energy of each of at least a portion of detected X-ray photons, and count the detected X-ray photons of different energy ranges.

In some embodiments, the imaging system may include a processing device. The processing device may be configured to, for each of the plurality of point radiation sources, determine a candidate image corresponding to the each point radiation source based on the energy range of the radiation beam emitted by the each point radiation source, energies of detected X-ray photons corresponding to the radiation beam, and the count of the detected X-ray photons corresponding to the radiation beam. The processing device may be configured to generate a target image based on the candidate images corresponding to the plurality of point radiation sources.

In some embodiments, the imaging system may be a digital breast tomosynthesis (DBT) system.

In some embodiments, the subject may be a breast. The imaging system may include a compression component located between the at least one array radiation source and the detector. The compression component may be configured to position the breast. The at least one array radiation source may include a linear array radiation source and a planar array radiation source. The linear array radiation source may include a plurality of first point radiation sources. The linear array radiation source may be configured on a chest-wall side of the breast. The planar array radiation source may include a plurality of second point radiation sources.

In some embodiments, an arrangement density of the plurality of first point radiation sources may be higher than an arrangement density of the plurality of second point radiation sources.

In some embodiments, the plurality of first point radiation sources may be arranged along a straight line.

In some embodiments, the linear array radiation source may form a radiation region. A first radiation surface in the radiation region formed by the linear array radiation source may be perpendicular to the compression component.

In some embodiments, the imaging system may include a first shielding component configured to prevent a radiation beam emitted by the planar array radiation source from traversing the radiation region.

In some embodiments, the first shielding component may be configured on the compression component. The first shielding component may be parallel to a second radiation surface in the radiation region formed by the linear array radiation source. The first radiation surface may be closer to the chest-wall side of the breast than the second radiation surface.

In some embodiments, the imaging system may include a first driving device configured to drive the first shielding component to move relative to the compression component.

In some embodiments, the imaging system may include a second shielding component configured to prevent a radiation beam emitted by the planar array radiation source or the linear array radiation source from traversing the chest-wall side of the breast.

In some embodiments, the second shielding component may be configured on an end of the compression component.

In some embodiments, the imaging system may include a third shielding component configured on at least one of a side perpendicular to the chest-wall side of the breast or a side opposite to the chest-wall side of the breast.

In some embodiments, the imaging system may include a second driving device configured to drive the detector to move relative to the at least one array radiation source.

According to another aspect of the present disclosure, an imaging method may be implemented on a computing device having at least one processor and at least one storage device. The imaging method may include providing a medical device including at least one array radiation source. The imaging method may include obtaining, based on information of a subject to be scanned by the medical device, at least one parameter of the at least one array radiation source of the medical device. The imaging method may include causing the medical device to perform a scan on the subject based on the at least one parameter of the at least one array radiation source. The imaging method may include generating an image of the subject based on the scan.

In some embodiments, the at least one array radiation source may include a plurality of point radiation sources. The at least one parameter of the array radiation source may include at least one of a position of the array radiation source, a position of one of the plurality of point radiation sources, or a radiation dose of a radiation beam emitted by one of the plurality of point radiation sources.

According to another aspect of the present disclosure, an imaging method may be implemented on a computing device having at least one processor and at least one storage device. The imaging method may include causing each point radiation source of a plurality of point radiation sources of an array radiation source to simultaneously emit a radiation beam to a subject. Each radiation beam may include a plurality of X-ray photons. The subject may be located between the array radiation source and a detector. At least two radiation beams emitted by the plurality of point radiation sources may be different. The imaging method may include, for each of the plurality of point radiation sources, obtaining, by the detector, energies of detected X-ray photons corresponding to the radiation beam emitted by the each point radiation source and a count of the detected X-ray photons corresponding to the radiation beam. The imaging method may include determining a candidate image corresponding to the each point radiation source based on an energy range of the radiation beam emitted by the each point radiation source, the energies of the detected X-ray photons corresponding to the radiation beam, and the count of detected X-ray photons corresponding to the radiation beam. The imaging method may include generating a target image based on the candidate images corresponding to the plurality of point radiation sources.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 15 is a flowchart illustrating an exemplary process for generating a target image according to some embodiments of the present disclosure.

DETAILED DESCRIPTION

Figure 1:
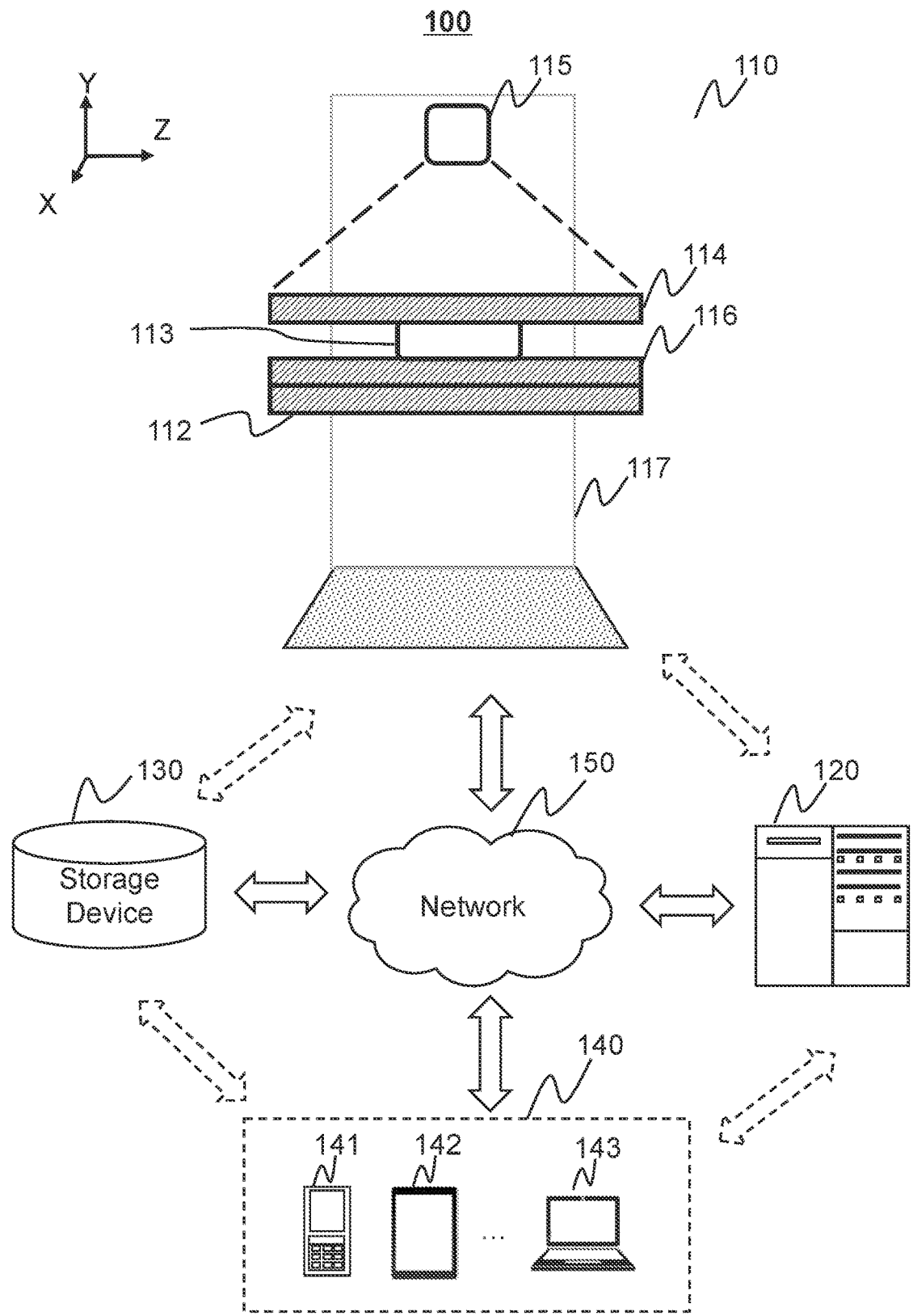
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

Provided herein are systems and components for a medical system. The medical system may include an imaging device, a treatment device, or a combination thereof. In some embodiments, the medical system may include a single modality imaging system and/or a multi-modality imaging system. The single modality imaging system may include, for example, a digital breast tomosynthesis (DBT) device, a computed tomography (CT) device, a cone beam computed tomography (CBCT) device, a digital subtraction angiography (DSA), a positron emission tomography (PET) device, a single-photon emission computed tomography (SPECT) device, a magnetic resonance imaging (MRI) device (also referred to as an MR device, an MR scanner), an ultrasonography scanner, a digital radiography (DR) scanner, or the like, or any combination thereof. The multi-modality imaging system may include, for example, a positron emission tomography-X-ray imaging (PET-X-ray) system, a single photon emission computed tomography-magnetic resonance imaging (SPECT-MRI) system, a positron emission tomography-computed tomography (PET-CT) system, a digital subtraction angiography-magnetic resonance imaging (DSA-MRI) system, etc. For illustration purposes, the present disclosure is described with reference to a DBT device. It should be noted that the imaging system described below is merely provided for illustration purposes, and not intended to limit the scope of the present disclosure.

An aspect of the present disclosure relates to an imaging system. The imaging system may include at least one array radiation source and a detector. The array radiation source may include a planar array radiation source and/or a linear array radiation source. Each array radiation source may include a plurality of point radiation sources. The at least one array radiation source may be configured to emit at least one radiation beam. The detector may be configured to detect at least part of the at least one radiation beam.

In some embodiments, the imaging system may include a compression component located between the at least one array radiation source and the detector, and the at least one array radiation source may include a linear array radiation source and a planar array radiation source. The imaging system may further include at least one shielding component configured to block a pathway of radiation emitted by a radiation source so that the radiation does not reach or traverse a certain region of the radiation system. For instance, the imaging system may further include a first shielding component, a second shielding component, and/or a third shielding component. The first shielding component may be configured to prevent a radiation beam emitted by the planar array radiation source from traversing a radiation region formed by the linear array radiation source. The second shielding component may be configured to prevent a radiation beam emitted by the planar array radiation source and/or the linear array radiation source from traversing a chest-wall side of a breast of a patient. The third shielding component may be configured on at least one of a side perpendicular to the chest-wall side of the breast or a side opposite to the chest-wall side of the breast. The third shielding component may be configured to prevent a radiation beam emitted by the planar array radiation source and/or the linear array radiation source from traversing or irradiating a region (e.g., an arm, the abdomen) other than the breast of the patient, and/or a user (e.g., a doctor) of the medical device.

Another aspect of the present disclosure relates to an imaging method. The method may include providing a medical device including at least one array radiation source. The method may also include obtaining, based on information of a subject to be scanned by the medical device, at least one parameter of the at least one array radiation source of the medical device. The method may also include causing the medical device to perform a scan on the subject based on the at least one parameter of the array radiation source. The method may further include generating an image of the subject based on the scan.

Another aspect of the present disclosure relates to an imaging method. The method may include causing each point radiation source of a plurality of point radiation sources of an array radiation source to simultaneously emit a radiation beam to a subject. Each radiation beam may include a plurality of X-ray photons. The subject may be located between the array radiation source and a detector. At least two radiation beams emitted by the plurality of point radiation sources may be different in terms of energy. The method may also include, for each of the plurality of point radiation sources, obtaining, by the detector, energies of detected X-ray photons corresponding to the radiation beam emitted by the each point radiation source and a count of the detected X-ray photons corresponding to the radiation beam. The method may also include determining a candidate image corresponding to the each point radiation source based on an energy range of the radiation beam emitted by the each point radiation source, the energies and the count of the detected X-ray photons corresponding to the radiation beam. The method may further include generating a target image based on the candidate images corresponding to the plurality of point radiation sources.

Accordingly, during a scan of a subject by the medical device, a plurality of point radiation sources of an array radiation source of the medical device may emit a plurality of radiation beams to the subject from different directions when the position of the array radiation source is fixed. Therefore, the effective focal spot size of the array radiation source may be reduced, and the quality of a reconstructed image of the subject may be improved, which, in turn, may increase the efficiency and/or accuracy of a diagnosis performed on the basis of the reconstructed image. The scanning time may be reduced due to the use of the plurality of point radiation sources, the probability and/or extent of movement of the subject during the scan may be reduced, and a motion blur in the reconstructed image caused by the movement of the subject may be avoided or reduced. In addition, the scanning efficiency of the medical device may be improved, which may further improve the efficiency of a user (e.g., a doctor) of the medical device.

FIG. 1 is a schematic diagram illustrating an exemplary medical system according to some embodiments of the present disclosure. As illustrated, a medical system 100 may include a medical device 110, a processing device 120, a storage device 130, a terminal 140, and a network 150. The components of the medical system 100 may be connected in one or more of various ways. Merely by way of example, as illustrated in FIG. 1, the medical device 110 may be connected to the processing device 120 directly as indicated by the bi-directional arrow in dotted lines linking the medical device 110 and the processing device 120, or through the network 150. As another example, the storage device 130 may be connected to the medical device 110 directly as indicated by the bi-directional arrow in dotted lines linking the medical device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The medical device 110 may be configured to acquire data relating to a subject 113. The medical device 110 may scan the subject 113 or a portion thereof that is located within its detection region and generate imaging data relating to the subject 113 or the portion thereof. The imaging data relating to at least one part of the subject 113 may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. The subject 113 may be biological or non-biological. For example, the subject 113 may include a patient, a man-made object, etc. As another example, the subject 113 may include a specific portion, an organ, and/or tissue of the patient. Specifically, the subject 113 may include the head, the neck, a breast, the thorax, the heart, the stomach, a blood vessel, soft tissue, a tumor, or the like, or any combination thereof. In the present disclosure, "object" and "subject" are used interchangeably.

In some embodiments, the medical device 110 may include a single modality imaging device. For example, the medical device 110 may include a digital breast tomosynthesis (DBT) device, a computed tomography (CT) device, a cone beam computed tomography (CBCT) device, a digital subtraction angiography (DSA), a positron emission tomography (PET) device, a single-photon emission computed tomography (SPECT) device, a magnetic resonance imaging (MRI) device (also referred to as an MR device, an MR scanner), an ultrasonography scanner, a digital radiography (DR) scanner, or the like, or any combination thereof. In some embodiments, the medical device 110 may include a multi-modality imaging device. Exemplary multi-modality imaging devices may include a PET-CT device, a PET-MR device, or the like, or a combination thereof.

Merely by way of example, the medical device 110 may be a DBT device. The DBT device may include a detector 112, a compression component 114, a radiation source 115, a holder 116, and a gantry 117. The gantry 117 may be configured to support one or more components (e.g., the detector 112, the compression component 114, the radiation source 115, the holder 116) of the medical device 110.

The radiation source 115 may include a high voltage generator (not shown in FIG. 1), a tube (not shown in FIG. 1), and a collimator (not shown in FIG. 1). The high voltage generator may be configured to generate a high-voltage for the tube. The tube may be configured to generate and/or emit a radiation beam based on the high-voltage. The radiation beam may include a particle ray, a photon ray, or the like, or a combination thereof. In some embodiments, the radiation beam may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. In some embodiments, the radiation source 115 may include at least one array radiation source. The array radiation source may include a planar array radiation source (e.g., a planar array radiation source 618 illustrated in FIGS. 6 and 7) and/or a linear array radiation source (e.g., a linear array radiation source 518 illustrated in FIGS. 5A and 5B). For example, the radiation source 115 may include one or more linear array radiation sources and/or one or more planar array radiation sources. More descriptions of the array radiation source may be found elsewhere in the present disclosure (e.g., FIGS. 3-12C and the descriptions thereof). The collimator may be configured to control an irradiation region (i.e., a radiation field) on the subject 113.

The detector 112 may be configured to detect at least part of the radiation beam. In some embodiments, the detector 112 may be configured opposite to the radiation source 115. For example, the detector 112 may be configured in a direction (substantially) perpendicular to a central axis of the radiation beam emitted by the radiation source 115. As used herein, "substantially" indicates that the deviation is below a threshold (e.g., 5%, 10%, 15%, 20%, 30%, etc.). For instance, a direction being substantially perpendicular to an axis (or another direction) indicates that the deviation of the angle between the direction and the axis (or the other direction) from a right angle is below a threshold. Merely by way of example, a direction being substantially perpendicular to an axis (or another direction) indicates that the angle between the direction and the axis (or the other direction) is in the range of 70°-110°, or 80°-100°, or 85°-95°, etc. As another example, a direction being substantially parallel to an axis (or another direction) indicates that the deviation of the angle between the direction and the axis (or the other direction) from zero degrees is below a threshold. Merely by way of example, a direction being substantially parallel to an axis (or another direction) indicates that the angle between the direction and the axis (or the other direction) is below 30°, or below 25°, or below 20°, or below 15°, or below 10°, or below 5°, etc. In some embodiments, the detector 112 may include a plurality of detecting units. The plurality of detecting units of the detector 112 may be arranged in any suitable manner, for example, a single row, two rows, or another number of rows. The detector 112 may include a scintillation detector (e.g., a cesium iodide detector), a gas detector, a flat panel detector, or the like. In some embodiments, the detector 112 may include a photon counting detector. The photon counting detector may detect an energy of a detected X-ray photon and the count detected X-ray photons. For example, a photomultiplier tube configured on the detector 112 (e.g., the photon counting detector) may be configured to count the detected X-ray photons of different energy ranges.

In some embodiments, the radiation source 115 may rotate around a rotation axis during a scan such that the subject 113 may be scanned (imaged and/or treated) from a plurality of directions. Merely by way of example, the radiation source 115 may be fixedly or moveably attached to the gantry 117, and the detector 112 may be fixedly or flexibly attached to the gantry 117 opposite to the radiation source 115. As used herein, a fixed attachment of component A (e.g., the radiation source 115) to component B (e.g., the gantry 117) indicates that the component A does not move relatively to the component B when the component A and the component B are properly assembled and used as intended. As used herein, a moveable attachment of component A (e.g., the radiation source 115) to component B (e.g., the gantry 117) indicates that the component A can move relatively to the component B when the component A and the component B are properly assembled and used as intended. When the gantry 117 rotates about a gantry rotation axis, the radiation source 115 and the detector 112 attached on the gantry 117 may rotate along with the gantry 117, and the subject 113 may be scanned from a plurality of gantry angles. The gantry rotation axis of the gantry 117 may be in the direction of the X-axis as illustrated in FIG. 1. As used herein, a gantry angle relates to a position of the radiation source 115 with reference to the medical device 110. For example, a gantry angle may be an angle between a vertical direction and a direction of a beam axis of a radiation beam emitted from the radiation source 115 of the medical device 110. In some embodiments, a driving device (e.g., a motor, a hydraulic cylinder) may be connected to the gantry 117 to drive the gantry 117 to move (e.g., rotate, translate).

The holder 116 and the compression component 114 may be configured to position the subject 113 (e.g., a breast). In some embodiments, the holder 116 and/or the compression component 114 may be fixedly or moveably attached to the gantry 117. The holder 116 may be placed on the top of the detector 112. The subject 113 may be placed on the holder 116. For example, a patient may lay her breast on the holder 116. The compression component 114 may be located between the radiation source 115 and the holder 116. For reasons related both to the immobilizing of the subject 113 (e.g., the breast) and to image quality or intensity of X-rays delivered to the subject 113 (e.g., the breast), By compressing the subject 113 (e.g., the breast) during a scan of the subject 113, the subject 113 may be immobilized during the scan, and the intensity of X-rays delivered to the subject 113 may be increased due to the reduced volume of the subject 113, thereby improving the quality of an image of the subject 113 so acquired. The compression force may be applied through the compression component 114 that compresses the subject 113 (e.g., the breast) on the holder 116. After the breast is compressed by the compression component 114, the shape of the compressed breast may be relatively thin and uniform, and soft tissues in the compressed breast may be separated, which may further improve the quality of an image of the breast so acquired. In some embodiments, the compression component 114 and the holder 116 may not block the radiation beams emitted by the radiation source 115.

During the scan of the subject 113 (e.g., the breast), X-rays emitted by the radiation source 115 may traverse the subject 113 (e.g., the breast). The detector 112 located opposite to the radiation source 115 may detect at least a portion of the X-rays that have traversed the subject 113 (e.g., the breast) and the holder 116. The detector 112 may transform optical signals of the detected X-rays into digital signals, and transmit the digital signals to the processing device 120 for further processing (e.g., generating a breast image).

Figure 9:
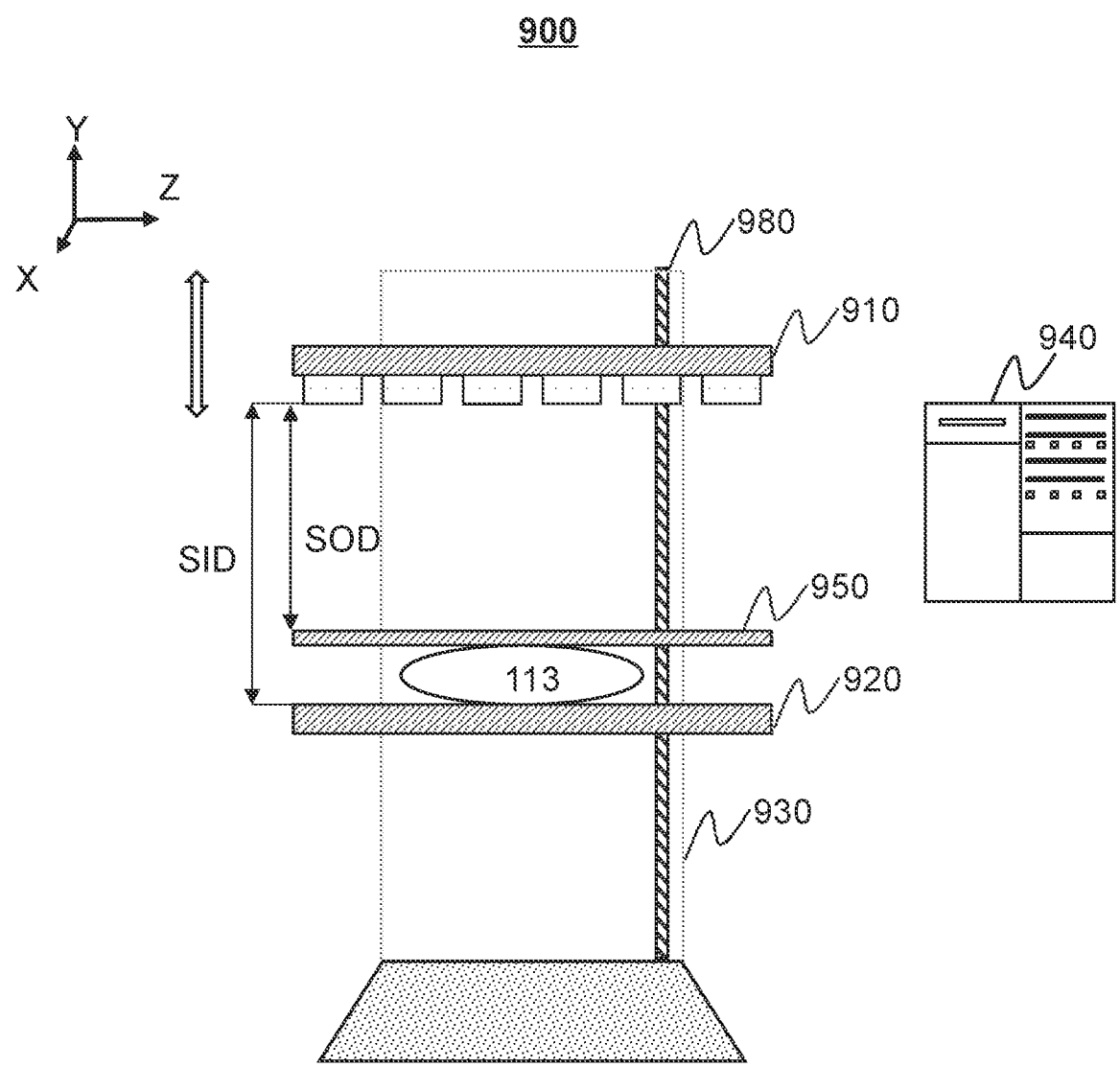
FIG. 9 is a schematic diagram illustrating an exemplary medical device according to some embodiments of the present disclosure.

In some embodiments, the radiation source 115, the detector 112, the holder 116, and/or the compression component 114 may move along a guide rail (e.g., a guide rail 980 shown in FIG. 9). For example, the radiation source 115 and/or the detector 112 may move along the guide rail to adjust a distance between the radiation source 115 and the detector 112. As another example, the holder 116 and/or the compression component 114 may move along the guide rail to position the subject 113 (e.g., a breast).

The processing device 120 may process data and/or information obtained from the medical device 110, the storage device 130, and/or the terminal(s) 140. For example, the processing device 120 may obtain, based on information of a subject (e.g., the subject 113) to be scanned by a medical device (e.g., the medical device 110), at least one parameter of an array radiation source (e.g., the radiation source 115) of the medical device. As another example, the processing device 120 may cause a medical device (e.g., the medical device 110) to perform a scan on a subject (e.g., the subject 113) based on at least one parameter of an array radiation source (e.g., the radiation source 115). As still another example, the processing device 120 may generate an image of a subject based on a scan of the subject. As still another example, the processing device 120 may cause multiple (some or all) point radiation source of a plurality of point radiation sources of an array radiation source (e.g., the radiation source 115) to simultaneously emit a radiation beam to a subject. As still another example, the processing device 120 may obtain energies of detected X-ray photons corresponding to a radiation beam emitted by a point radiation source and a count of the detected X-ray photons corresponding to the radiation beam from a detector (e.g., the detector 112). As still another example, the processing device 120 may determine a candidate image corresponding to each point radiation source of a plurality of point radiation sources of an array radiation source (e.g., the radiation source 115) based on energy range of a radiation beam emitted by the each point radiation source, energies of the detected X-ray photons corresponding to the radiation beam, and a count of detected X-ray photons corresponding to the radiation beam. As still another example, the processing device 120 may generate a target image based on candidate images corresponding to a plurality of point radiation sources of an array radiation source (e.g., the radiation source 115).

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical device 110.

The storage device 130 may store data, instructions, and/or any other information. In some embodiments, the storage device 130 may store data obtained from the medical device 110, the processing device 120, and/or the terminal(s) 140. The data may include image data acquired by the processing device 120, algorithms and/or models for processing the image data, etc. For example, the storage device 130 may store an image of a subject obtained from a medical device (e.g., the medical device 110). As still another example, the storage device 130 may store at least one parameter of an array radiation source (e.g., the radiation source 115) of a medical device (e.g., the medical device 110) determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140). One or more components in the medical system 100 may access the data or instructions stored in the storage device 130 via the network 150. In some embodiments, the storage device 130 may be integrated into the medical device 110.

The terminal(s) 140 may be connected to and/or communicate with the medical device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 and/or the terminal 140 may obtain an image from the medical device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

In the present disclosure, the X axis, the Y axis, and the Z axis shown in FIG. 1 may form an orthogonal coordinate system. The X axis and the Z axis shown in FIG. 1 may be in a horizontal plane, and the Y axis may be perpendicular to the horizontal plane. As illustrated, the positive X direction along the X-axis may be from the left side to the right side of the medical device 110 seen from the direction facing the front of the medical device 110; the positive Y direction along the Y-axis shown in FIG. 1 may be from the lower part to the upper part of the medical device 110 (or from the floor to the ceiling of the room where the medical device 110 is located); and the X-axis shown in FIG. 1 may be perpendicular to the Z-axis and the Y-axis.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, two or more components of the medical system 100 may be integrated into a single component. For example, the holder 116 and the detector 112 may be integrated into a single component. As another example, the holder 116 may be omitted, and the subject 113 may be placed on the detector 112. A component of the medical system 100 may be implemented on two or more sub-components. Additionally or alternatively, the medical system 100 may include one or more additional components and/or one or more components of the medical system 100 described above may be omitted. In some embodiments, the medical system 100 may include a control device (e.g., a control device 940 illustrated in FIG. 9) configured to control one or more components (e.g., the detector 112, the compression component 114, the radiation source 115, the holder 116, the gantry 117) of the medical system 100. For example, the control device may be configured to control the radiation source 115 to move along a guide rail (e.g., the guide rail 980 shown in FIG. 9) to adjust a distance between the radiation source 115 and the detector 112. As another example, the control device may be configured to adjust at least one parameter of the radiation source 115 (e.g., an array radiation source). The at least one parameter of the array radiation source may include a position of the array radiation source, a position of at least one of a plurality of point radiation sources of the array radiation source, an orientation of the at least one of the plurality of point radiation sources of the array radiation source, a radiation dose of a radiation beam, or the like, or any combination thereof. More descriptions of the at least one parameter of the array radiation source may be found elsewhere in the present disclosure (e.g., FIG. 14, and descriptions thereof). As still another example, the control device may be configured to control a high-voltage generated by the high voltage generator or an energy range of a radiation beam generated by the tube of the radiation source 115. More descriptions of the control device may be found elsewhere in the present disclosure (e.g., FIG. 9, and descriptions thereof).

As another example, the radiation source 115 may include a filtering device (e.g., a filtering device 840 illustrated in FIG. 8) configured to absorb a radiation beam whose energy level is below a preset energy range or threshold. As still another example, the medical device 110 may include one or more shielding components (e.g., a first shielding component 1060, a second shielding component 1050, and a third shielding component 1070 illustrated in FIG. 10) and/or one or more driving devices. More descriptions of the filtering device, the shielding component(s), and the driving device may be found elsewhere in the present disclosure (e.g., FIGS. 8-12 and descriptions thereof).

Figure 2:
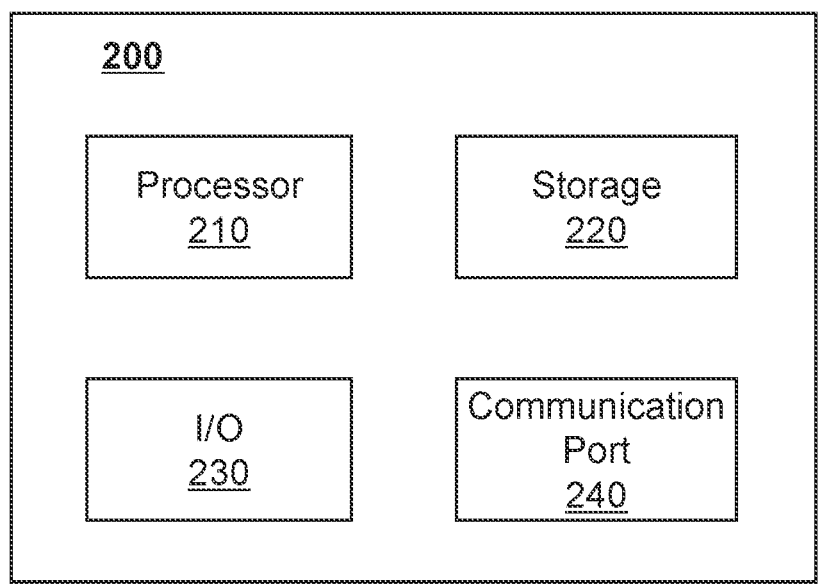
FIG. 2 is a schematic diagram illustrating exemplary hardware and/or software components of an exemplary computing device on which the processing device may be implemented according to some embodiments of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process imaging data obtained from the medical device 110, the terminal(s) 140, the storage device 130, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the medical device 110, the terminal(s) 140, the storage device 130, and/or any other component of the medical system 100. The storage 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the medical device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
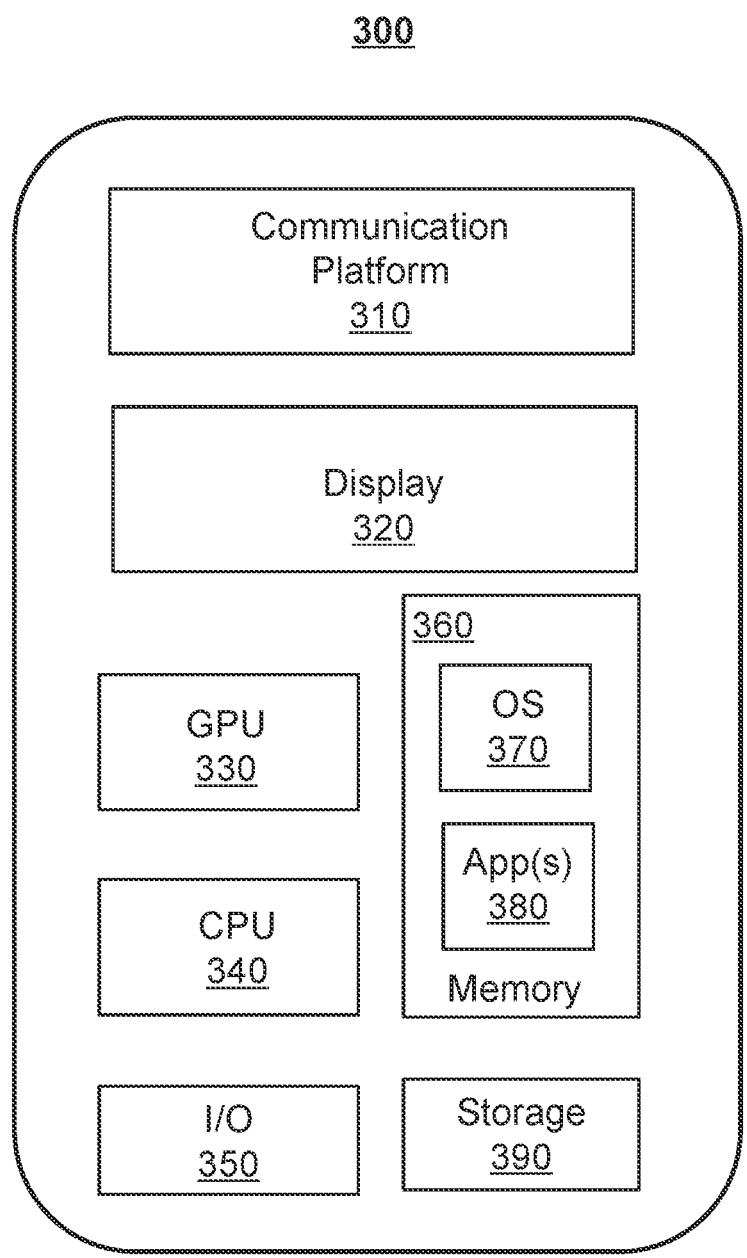
FIG. 3 is a schematic diagram illustrating exemplary hardware and/or software components of an exemplary mobile device on which the terminal(s) may be implemented according to some embodiments of the present disclosure.

FIG. 3 is a schematic diagram illustrating exemplary hardware and/or software components of an exemplary mobile device 300 according to some embodiments of the present disclosure. In some embodiments, a terminal(s) 140 and/or a processing device 120 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the medical system 100, and enable data and/or signal to be transmitted between the mobile device 300 and other components of the medical system 100. For example, the communication platform 310 may establish a wireless connection between the mobile device 300 and the medical device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the medical system 100. For example, the communication platform 310 may transmit data and/or signals inputted by a user to other components of the medical system 100. The inputted data and/or signals may include a user instruction. As another example, the communication platform 310 may receive data and/or signals transmitted from the processing device 120. The received data and/or signals may include imaging data acquired by a detector of the medical device 110.

In some embodiments, a mobile operating system (OS) 370 (e.g., iOS™, Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information from the processing device 120. User interactions with the information stream may be achieved via the I/O 350 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
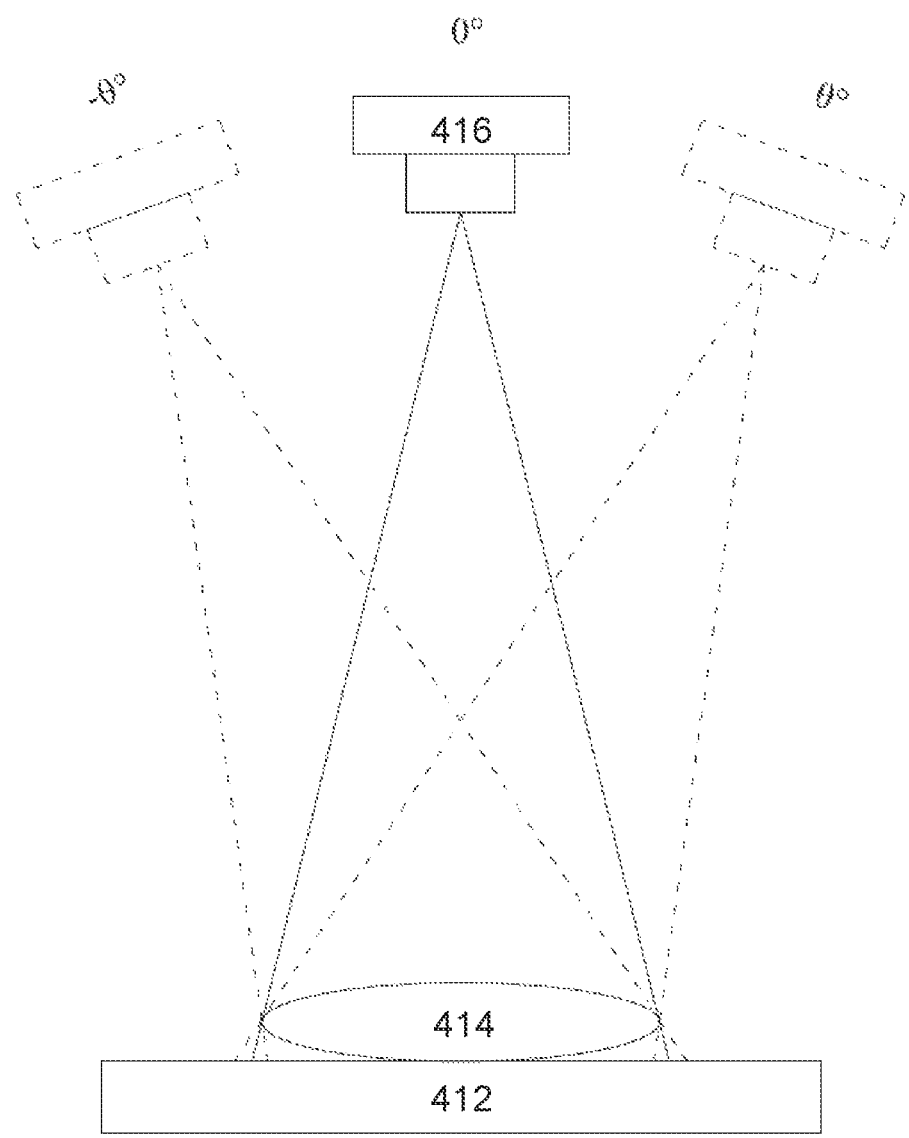
FIG. 4 is a schematic diagram illustrating a prior art radiation source of a medical device.

FIG. 4 is a schematic diagram illustrating a prior art radiation source of a medical device. As illustrated in FIG. 4, a medical device 400 (e.g., a DBT device) may include a radiation source 416 and a detector 412.

The radiation source 416 may be configured to generate and/or emit a radiation beam. The detector 412 may be configured to detect at least part of the radiation beam. In some embodiments, the radiation source 416 may rotate about a rotation axis during a scan such that a subject 414 may be scanned (imaged and/or treated) from a plurality of directions. For example, the radiation source 416 may be fixedly or moveably attached to a gantry (not shown in FIG. 4), and the detector 412 may be fixedly or moveably attached to the gantry opposite to the radiation source 416. When the gantry rotates about a gantry rotation axis, the radiation source 416 and the detector 412 attached on the gantry may rotate along with the gantry, and the subject 414 may be imaged and/or treated from a plurality of gantry angles.

Merely by way of example, the subject 414 may be scanned from a first gantry angle, a second gantry angle, and a third gantry angle. A first difference between the first gantry angle and the second gantry angle may be the same as or different from a second difference between the second gantry angle and the third gantry angle. The first difference and/or the second difference may be in a range from 0° to 360°. Merely by way of example, as illustrated in FIG. 4, the first gantry angle may be −θ°, the second gantry angle may be 0°, and the third gantry angle may be θ°.

Accordingly, the subject 414 may be scanned from the plurality of directions by rotating the radiation source 416 of the prior art medical device 400 (e.g., the DBT device). The movement of the radiation source 416 may affect the effective focal spot size of the radiation source 416, and the quality of a reconstructed image of the subject 414. The faster the moving speed of the radiation source 416, the larger the effective focal spot size of the radiation source 416, and the higher the blurring degree of edges of the reconstructed image of the subject 414. In addition, the movement of the radiation source 416 may lead to a long scanning time and reduce the scanning efficiency. The subject 414 (e.g., a patient) may also move during the scan, which may result in a motion blur in the reconstructed image, thereby further reducing the quality of the reconstructed image.

Figure 5A:
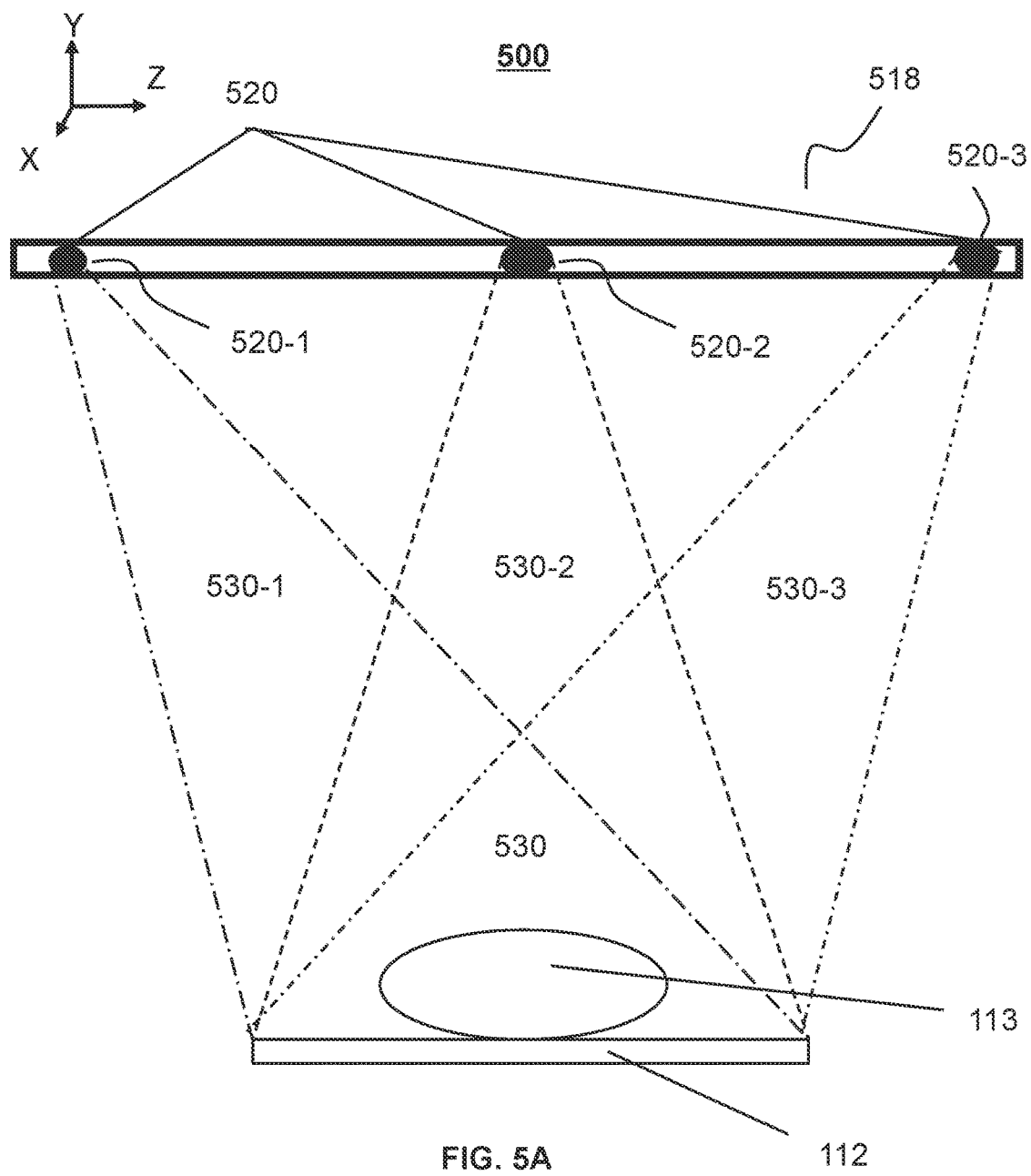
FIGS. 5A and 5B are schematic diagrams illustrating an exemplary linear radiation source of a medical device according to some embodiments of the present disclosure.
Figure 5B:
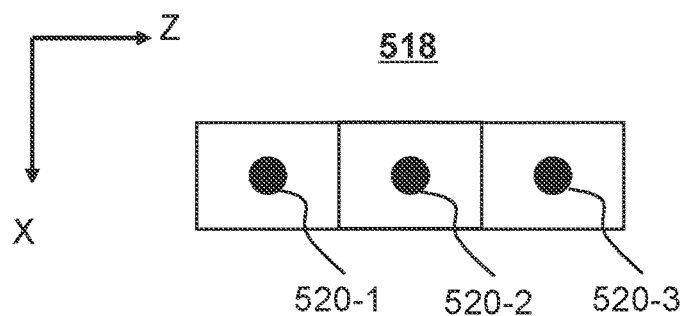

FIGS. 5A and 5B are schematic diagrams illustrating an exemplary linear radiation source of a medical device according to some embodiments of the present disclosure.

As illustrated in FIG. 5A, a medical device 500 (e.g., a DBT device) may include a linear array radiation source 518 and the detector 112. The linear array radiation source 518 may include a plurality of point radiation sources 520. The plurality of point radiation sources 520 may be arranged in a line (e.g., a straight line, a curved line, a polyline). Merely by way of example, a first point radiation source 520-1, a second point radiation source 520-2, and a third point radiation source 520-3 may be arranged in a straight line along the Z-axis direction as illustrated in FIGS. 5A and 5B (the same as the Z-axis direction as illustrated in FIG. 1).

In some embodiments, during a scan, the subject 113 may be positioned in an overlapping region 530 of a plurality of radiation regions of the plurality of point radiation sources 520 (e.g., a first radiation region 530-1 of the first point radiation source 520-1, a second radiation region 530-2 of the second point radiation source 520-2, a third radiation region 530-3 of the third point radiation source 520-3). Accordingly, a plurality of radiation beams emitted by the plurality of point radiation sources 520 may traverse the subject 113.

Figure 6:
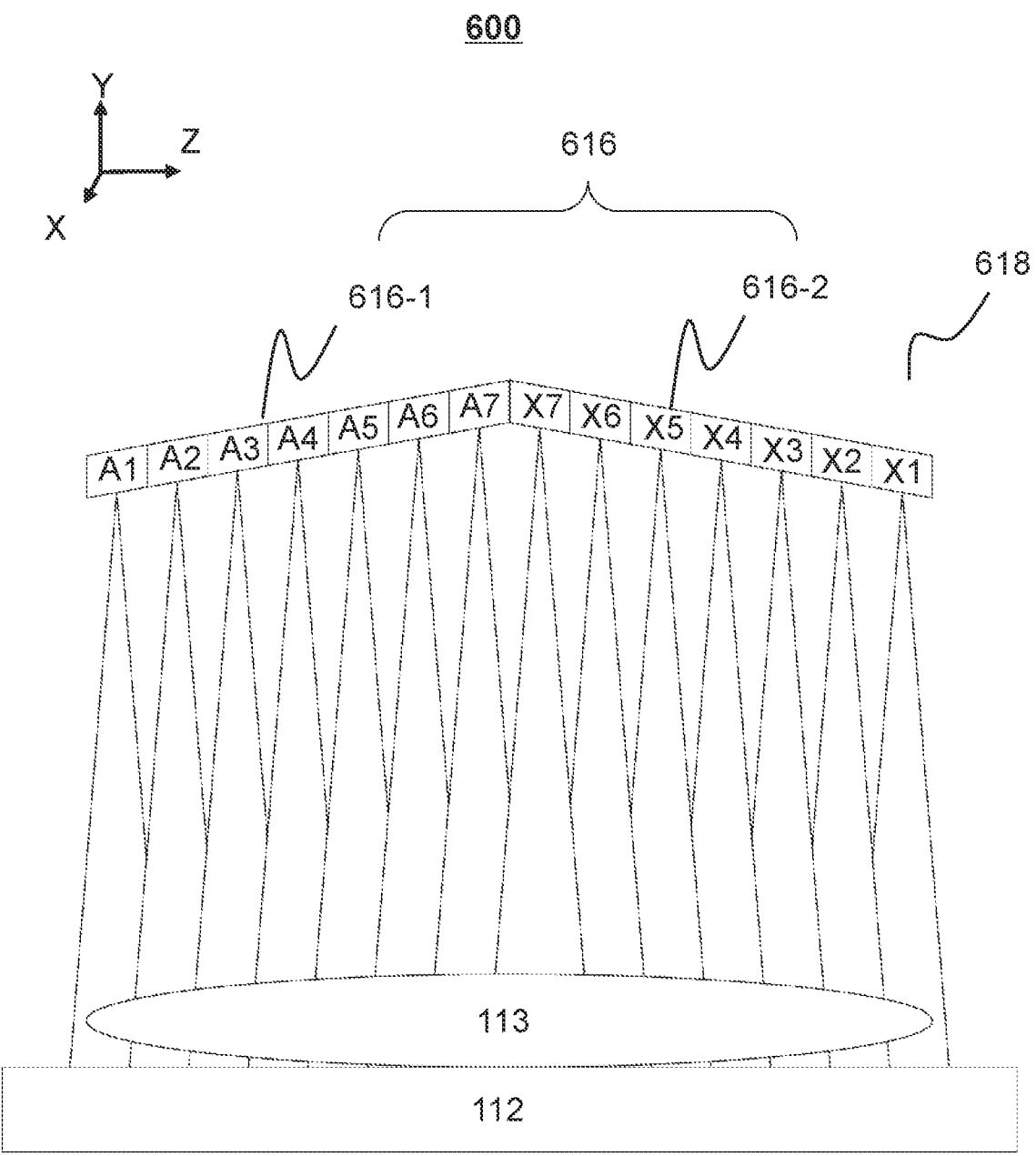
FIGS. 6 and 7 are schematic diagrams illustrating an exemplary planar array radiation source of a medical device according to some embodiments of the present disclosure.
Figure 7:
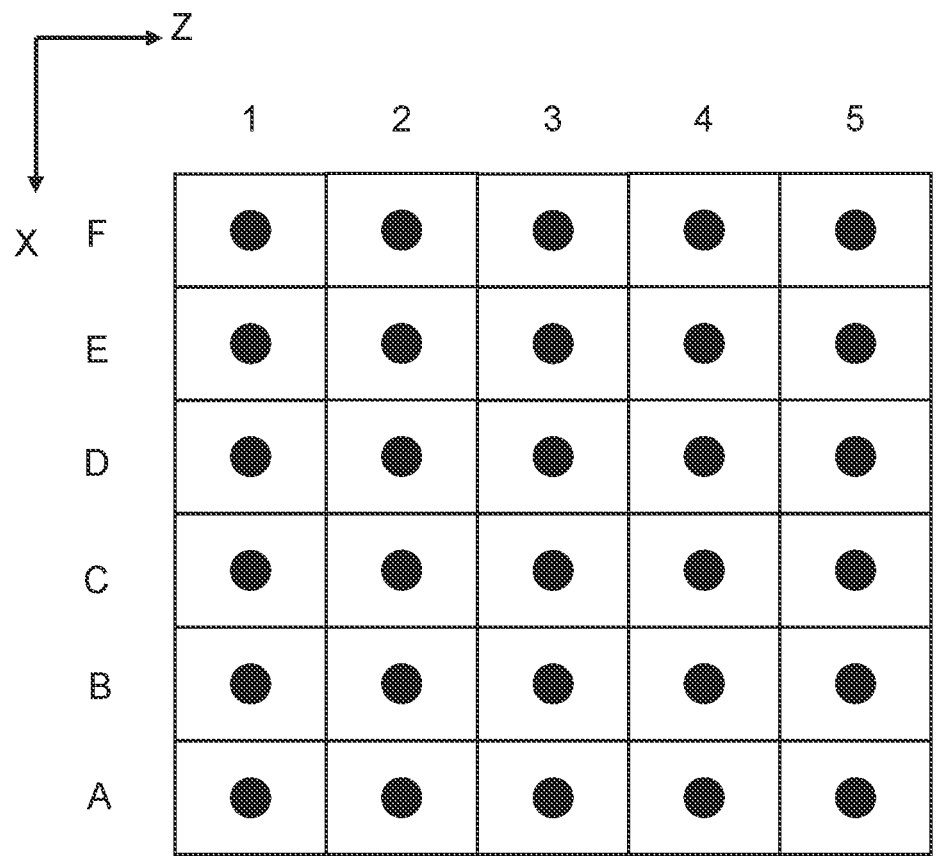

FIGS. 6 and 7 are schematic diagrams illustrating an exemplary planar array radiation source of a medical device according to some embodiments of the present disclosure.

As illustrated in FIG. 6, a medical device 600 (e.g., a DBT device) may include a planar array radiation source 618 and the detector 112. The planar array radiation source 618 may include at least one radiation source panel 616. The at least one radiation source panel 616 may be a flat panel or a curved panel. For example, the planar array radiation source 618 may include a first radiation source panel 616-1 and a second radiation source panel 616-2. The first radiation source panel 616-1 and the second radiation source panel 616-2 may be arranged at an angle. In some embodiments, the first radiation source panel 616-1 and the second radiation source panel 616-2 may be detached from each other. For example, the first radiation source panel 616-1 may be removably connected to the second radiation source panel 616-2. The angle between the first radiation source panel 616-1 and the second radiation source panel 616-2 may be adjustable. The range of the angle between the first radiation source panel 616-1 and the second radiation source panel 616-2 may be in the range from 140° to 180°, 130° to 180°, 120° to 180°, etc. The range of the angle between the first radiation source panel 616-1 and the second radiation source panel 616-2 may be 180° or less, e.g., 120°, 130°, 140°, 150°, 160°, etc.

In some embodiments, a plurality of point radiation sources (e.g., point radiation sources A1, A2, A3, . . . , F3, F4, F5 as illustrated in FIG. 7) may be configured on the radiation source panel 616. In some embodiments, the plurality of point radiation sources may form a two-dimensional array of point radiation sources. For example, the plurality of point radiation sources of the radiation source panel 616 may form a plurality of radiation source rows (e.g., a row A, a row B, . . . , a row F) each of which includes multiple point radiation sources arranged in the X-axis direction, and a plurality of radiation source columns (e.g., a column 1, a column 2, . . . , a column 5) each of which includes multiple point radiation sources arranged in the Z-axis direction, as illustrated in FIG. 7. Merely by way of example, the array of point radiation sources may have a configuration of 5×6 (5 columns by 6 rows) point radiation sources.

In some embodiments, the plurality of point radiation sources may be detachably configured on the radiation source panel 616. For example, the plurality of point radiation sources may be removably connected to the radiation source panel 616, which may facilitate the installation, maintenance, and/or replacement of the plurality of point radiation sources. Merely by way of example, if a point radiation source is broken, only that point radiation source or a small group (not the entire radiation source panel 616, or the entire radiation source panel 616-1 or 616-2) of point radiation sources including the broken point radiation source needs to be replaced.

In some embodiments, the plurality of point radiation sources may emit a plurality of radiation beams to the subject 113 from different directions. In some embodiments, at least two radiation beams emitted by the plurality of point radiation sources may be of different radiation angles. As used herein, a radiation angle of a point radiation source refers an angle between a vertical direction and a direction of a beam axis of a radiation beam emitted from the point radiation source. In some embodiments, an orientation of the point radiation source may be fixed. For example, one point radiation source may correspond to one radiation angle. In some embodiments, a point radiation source may rotate such that the orientation of the point radiation source may be adjustable. For example, one point radiation source may correspond to two or more radiation angles. In some embodiments, the plurality of point radiation sources may scan the subject 113 in a plurality of planes. For example, the point radiation sources A1, A2, A3, A4, and A5 may scan the subject 113 in a first plane, and the point radiation sources F1, F2, F3, F4, and F5 may scan the subject 113 in a second plane.

In some embodiments, each point radiation source of the plurality of point radiation sources may emit a radiation beam. At least two radiation beams emitted by the point radiation sources may be of different energy ranges. In some embodiments, a plurality of energy ranges of a plurality of radiation beams emitted by the plurality of point radiation sources may not overlap. As used herein, that a first energy range and a second energy range do not overlap refers to that the maximum energy value in the first energy range is less than the minimum energy value in the second energy range, wherein the first energy range is lower than the second energy range. For example, a first energy range of a first radiation beam emitted by a first point radiation source (e.g., the first point radiation source 520-1 illustrated in FIGS. 5A and 5B) may be 15~30 kilo-electron volts (keV), a second energy range of a second radiation beam emitted by a second point radiation source (e.g., the second point radiation source 520-2 illustrated in FIGS. 5A and 5B) may be 40~55 keV, and a third energy range of a third radiation beam emitted by a third point radiation source (e.g., the third point radiation source 520-3 illustrated in FIGS. 5A and 5B) may be 60~75 keV.

In some embodiments, a plurality of energy ranges of a plurality of radiation beams emitted by the plurality of point radiation sources may partially overlap. For example, a first energy range of a first radiation beam emitted by a first point radiation source (e.g., the first point radiation source 520-1 illustrated in FIGS. 5A and 5B) may be 15~32 keV, a second energy range of a second radiation beam emitted by a second point radiation source (e.g., the second point radiation source 520-2 illustrated in FIGS. 5A and 5B) may be 30~47 keV, and a third energy range of a third radiation beam emitted by a third point radiation source (e.g., the third point radiation source 520-3 illustrated in FIGS. 5A and 5B) may be 45~62 keV.

In some embodiments, if the plurality of energy ranges of the plurality of radiation beams emitted by the plurality of point radiation sources do not overlap, an energy difference between consecutive energy ranges is not less than an energy resolution of the detector. As used herein, an energy resolution of a detector measures its ability to distinguish X-rays with close energies. The better the energy resolution, the better it can separate two adjacent (e.g., consecutive) energy peaks, which allows identifying different decays or radionuclides in a spectrum. As used herein, two energy ranges are regarded as consecutive energy ranges in a plurality of energy ranges if the two energy ranges have consecutive rankings after the plurality of energy ranges are ranked based on energy values (e.g., the maximum energy value, the minimum energy value) of the plurality of energy ranges. For example, assuming that a first energy range is 15~30 keV, a second energy range is 40~55 keV, and a third energy range is 60~75 keV, the first energy range, the second energy range, and the third energy range may be ranked based on the maximum energy value in the first energy range (i.e., 30 keV), the maximum energy value in the second energy range (i.e., 55 keV), and the maximum energy value in the third energy range (i.e., 75 keV). That is, the first energy range, the second energy range, and the third energy range may be ranked as: the third energy range>the second energy range>the first energy range. In this case, the third energy range and the second energy range may be regarded as consecutive energy ranges, and the second energy range and the first energy range may be regarded as consecutive energy ranges.

In some embodiments, the point radiation source may include a cold cathode ray source (also referred to as a field electron emission cold cathode), a hot cathode ray source, or the like, or any combination thereof. The type of each point radiation source may be the same or different. As used herein, a cold cathode refers to a cathode that is not electrically heated by a filament. As used herein, a hot cathode refers to a cathode electrode which is heated to make it emit electrons due to thermionic emission. Compared to the hot cathode ray source, the operating temperature and the power consumption of the cold cathode ray source may be relatively low, and the time delay may be avoided or reduced. In addition, a spatial resolution of a reconstructed image generated by a medical device with the cold cathode ray source may be improved due to the lower operating temperature and the lower power consumption of the cold cathode ray source. In some embodiments, the point radiation source may be a monochromatic radiation source. As used herein, a monochromatic radiation source refers to that all waves generated by the radiation source have a same wavelength. For example, the plurality of point radiation sources may be monochromatic radiation sources of different colors, and accordingly the plurality of energy ranges of the plurality of radiation beams emitted by the plurality of point radiation sources may be different.

According to some embodiments of the present disclosure, during a scan of a subject by a medical device (e.g., the medical device 500, the medical device 600), a plurality of point radiation sources of an array radiation source (e.g., the linear array radiation source 518, the planar array radiation source 618) of the medical device may emit a plurality of radiation beams to the subject from different directions when the position of the array radiation source is fixed. Therefore, the effective focal spot size of the array radiation source may be reduced, and the quality of a reconstructed image of the subject may be improved. The scanning time may be reduced, the probability and/or the extent of movement of the subject during the scan may be reduced, and a motion blur in the reconstructed image caused by the movement of the subject may be avoided or reduced. Accordingly, the scanning efficiency of the medical device may be improved, which may further improve the diagnosis accuracy and the efficiency of a user (e.g., a doctor) of the medical device. In addition, compared with a prior art radiation source (e.g., the radiation source 416) shown in FIG. 4, more information of the subject may be obtained by using the array radiation source.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the plurality of point radiation sources of the planar array radiation source 618 may be arranged in an array of various shapes, such as a circular array, a square array, or a triangular array. In some embodiments, an array radiation source (e.g., the linear array radiation source 518, the planar array radiation source 618) may include any number (or count) of point radiation sources. The number (or count) of the point radiation sources may be determined based on actual needs (e.g., desired image quality, cost of the array radiation source). For example, if the desired image quality is relatively high, the number (or count) of the point radiation sources may be increased. If the cost of the array radiation source needs to be reduced, the number (or count) of the point radiation sources may be reduced.

Figure 8:
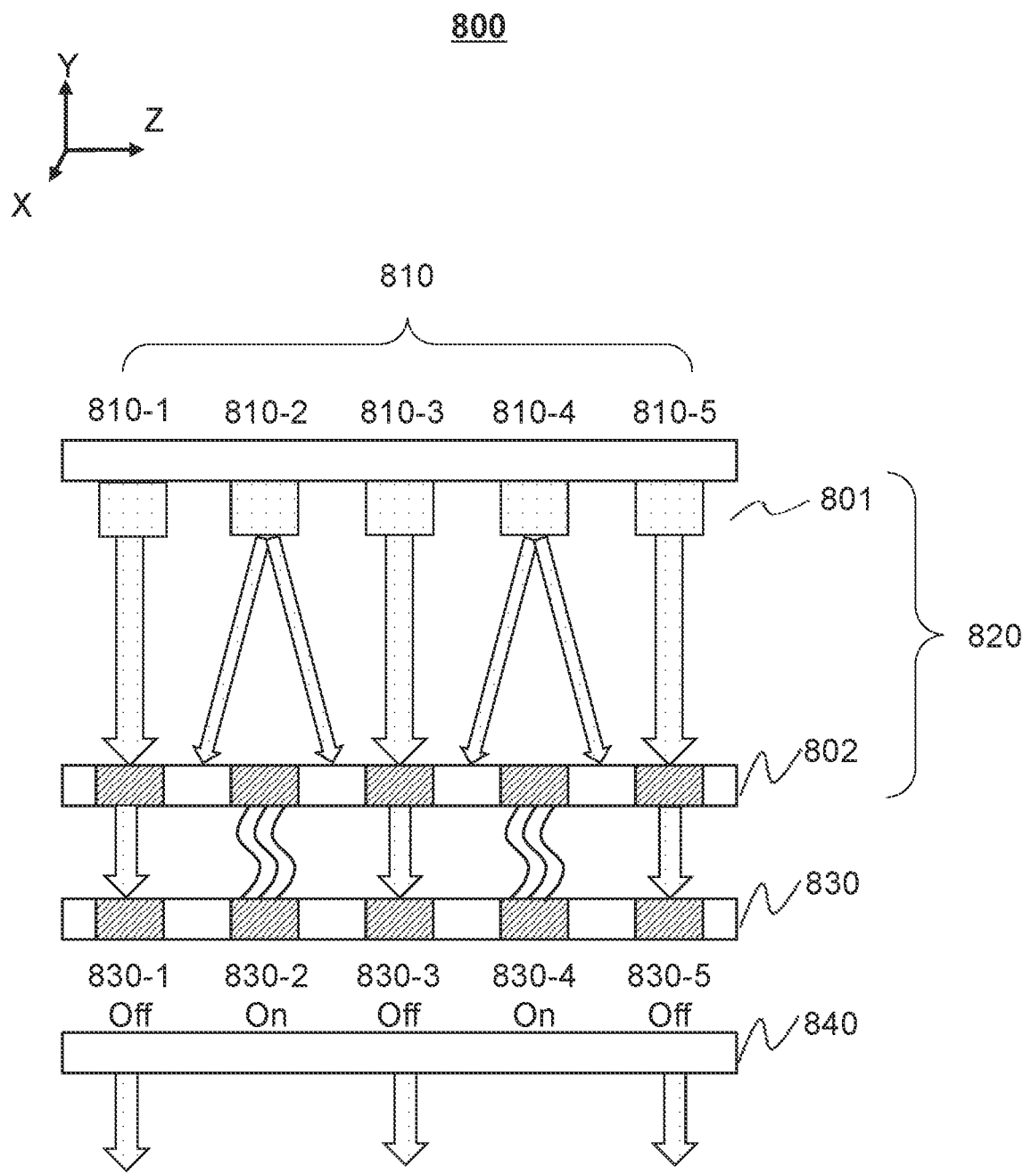
FIG. 8 is a schematic diagram illustrating an exemplary array radiation source according to some embodiments of the present disclosure.

FIG. 8 is a schematic diagram illustrating an exemplary array radiation source according to some embodiments of the present disclosure.

As illustrated in FIG. 8, an array radiation source 800 may include a plurality of point radiation source 810 (e.g., a point radiation source 801-1, a point radiation source 801-2, a point radiation source 801-3, a point radiation source 801-4, a point radiation source 801-5). Each point radiation source 810 may include a tube 820, an electromagnetic coil 830, and a filtering device 840. The tube 820 may include a filament 801 and an anode target 802. The filament 801 may be configured to generate electrons to bombard the anode target 802. The anode target 802 may be opposite to the filament 801, and configured to generate radiation beams (e.g., X-rays) when the electrons bombard the anode target 802. The filament 801 and the anode target 802 may be located in a vacuum. A relatively high energy of the electron beam generated by the filament 801 may correspond to a relatively high energy of a radiation beam generated by the anode target 802.

In some embodiments, the anode target 802 include a first region (e.g., a hatched region in 802 as illustrated in FIG. 8) and a second region (e.g., an open region in 802 as illustrated in FIG. 8). The first region of the anode target 802 may be made of a first material. The second region of the anode target 802 may be made of a second material. An atomic number of the first material may be higher than an atomic number of the second material. For example, the first material may include a high atomic number material, and the second material may include a low atomic number material. That is, the first material may be composed of an element with an atomic number greater than 18, and the second material may be composed of an element with an atomic number lower than 18. For example, the first material may include a metal, such as tungsten, molybdenum, copper, rhodium, silver, or the like, or an alloy thereof, or any combination thereof. The second material may include aluminum, or the like, or an alloy thereof, or any combination thereof. The first region of the anode target 802 may generate a radiation beam (e.g., an X-ray) with a relatively high energy when electrons bombard the first region of the anode target 802. The second region of the anode target 802 may generate a radiation beam (e.g., an X-ray) with a relatively low energy when electrons bombard the second region of the anode target 802.

The filtering device 840 may be configured to absorb a radiation beam lower than a preset energy range (or threshold). For example, most of the radiation beams (e.g., X-rays) generated by the second region of the anode target 802 may be absorbed by the filtering device 840, and most of the radiation beams (e.g., X-rays) generated by the first region of the anode target 802 may pass through the filtering device 840. The preset energy range may be determined based on the material and/or the structure of the filtering device 840. In some embodiments, the filtering device 840 may be made of a metal. For example, the filtering device 840 may be an aluminum slice, a copper slice, or the like. A relatively large thickness of the filtering device 840 may correspond to a relatively high preset energy range. As used herein, a thickness of the filtering device 840 refers to a dimension of the filtering device 840 along a Y-axis direction as illustrated in FIG. 8.

The electromagnetic coil 830 may be configured to control a moving direction of the radiation beam. In some embodiments, the electromagnetic coil 830 may generate a magnetic field to control the moving directions of the electrons generated by the filament 801. For example, if the electromagnetic coil 830 (e.g., an electromagnetic coil 830-1, an electromagnetic coil 830-3, an electromagnetic coil 830-5) is in an "off" state, that is, the electromagnetic coil 830 does not generate a magnetic field, the moving path of the electrons generated by the filament 801 of the point radiation source 810 (e.g., the point radiation source 801-1, the point radiation source 801-3, the point radiation source 801-5) does not bend, and the electrons may bombard a first region of the anode target 802. The first region of the anode target 802 may generate a radiation beam (e.g., an X-ray) with a relatively high energy (e.g., higher than the preset energy range of the filtering device 840). Most of the radiation beams (e.g., X-rays) generated by the first region of the anode target 802 may pass through the filtering device 840. Accordingly, the point radiation source 810 (e.g., the point radiation source 801-1, the point radiation source 801-3, the point radiation source 801-5) may emit the radiation beams (e.g., X-rays).

As another example, if the electromagnetic coil 830 (e.g., an electromagnetic coil 830-2, an electromagnetic coil 830-4) is in an "on" state, that is, the electromagnetic coil 830 generates a magnetic field, the moving path of the electrons generated by the filament 801 of the point radiation source 810 (e.g., the point radiation source 801-2, the point radiation source 801-4) may bend, and the electrons may bombard a second region of the anode target 802. The second region of the anode target 802 may generate a radiation beam (e.g., an X-ray) with a relatively low energy (e.g., lower than the preset energy range of the filtering device 840). Most of the radiation beams (e.g., X-rays) may be absorbed by the filtering device 840, and the point radiation source 810 (e.g., the point radiation source 801-2, the point radiation source 801-4) does not emit the radiation beams (e.g., X-rays).

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the electromagnetic coil 830 and/or the filtering device 840 may be omitted. As another example, the array radiation source 800 may include a high voltage generator (not shown in FIG. 8) configured to generate a high-voltage for the tube 820.

FIG. 9 is a schematic diagram illustrating an exemplary medical device according to some embodiments of the present disclosure.

As illustrated in FIG. 9, a medical device 900 may include an array radiation source 910, a detector 920, a gantry 930, a compression component 950, and a control device 940. The array radiation source 910 may be similar to the linear array radiation source 518 as described in connection with FIGS. 5A and 5B, the planer array radiation source 618 as described in connection with FIGS. 6 and 7, or the array radiation source 800 as described in connection with FIG. 8. The detector 920 may be similar to the detector 112 as described in connection with FIG. 1. The compression component 950 may be similar to the compression component 114 as described in connection with FIG. 1.

In some embodiments, the detector 920 may be fixedly attached to the gantry 930, and the array radiation source 910 may be flexibly attached to the gantry 930. For example, the array radiation source 910 may move along a guide rail 980 of the gantry 930 to adjust a source to image receptor distance (SID) and/or a source to object distance (SOD). As used herein, an SID refers to a distance between a focal spot target of a tube of a radiation source (e.g., the array radiation source 910) to an image receptor (e.g., the detector 920) along a beam axis of a radiation beam generated by and emitted from the tube. As used herein, an SOD refers to a distance between a focal spot target of a tube of a radiation source (e.g., the array radiation source 910) to a subject (e.g., the subject 113) to be scanned along a beam axis of a radiation beam generated by and emitted from the tube. In some embodiments the detector 920 may be flexibly attached to the gantry 930, and the array radiation source 910 may be fixedly attached to the gantry 930. For example, the detector 920 may move along the guide rail 980 of the gantry 930 to adjust the SID.

The control device 940 may be configured to control one or more components (e.g., the array radiation source 910, the detector 920, the gantry 930, the compression component 950) of the medical device 900. The control device 940 may control the one or more components (e.g., the array radiation source 910, the detector 920, the gantry 930, the compression component 950) of the medical device 900 automatically or according to a user instruction. In some embodiments, the control device 940 may control the detector 920 and/or the array radiation source 910 to move along the guide rail 980 to adjust the SOD and/or the SID. In some embodiments, the control device 940 may adjust at least one parameter of the array radiation source 910. More descriptions of the determination of the at least one parameter of the array radiation source may be found elsewhere in the present disclosure (e.g., FIG. 14, and descriptions thereof). In some embodiments, the control device 940 may control an energy range of a radiation beam generated by the array radiation source 910. For example, the control device 940 may control a high-voltage generated by a high voltage generator of the array radiation source 910. As another example, the control device 940 may control a power of the array radiation source 910.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the control device 940 and the processing device 120 illustrated in FIG. 1 may be integrated into a single component.

Figure 10:
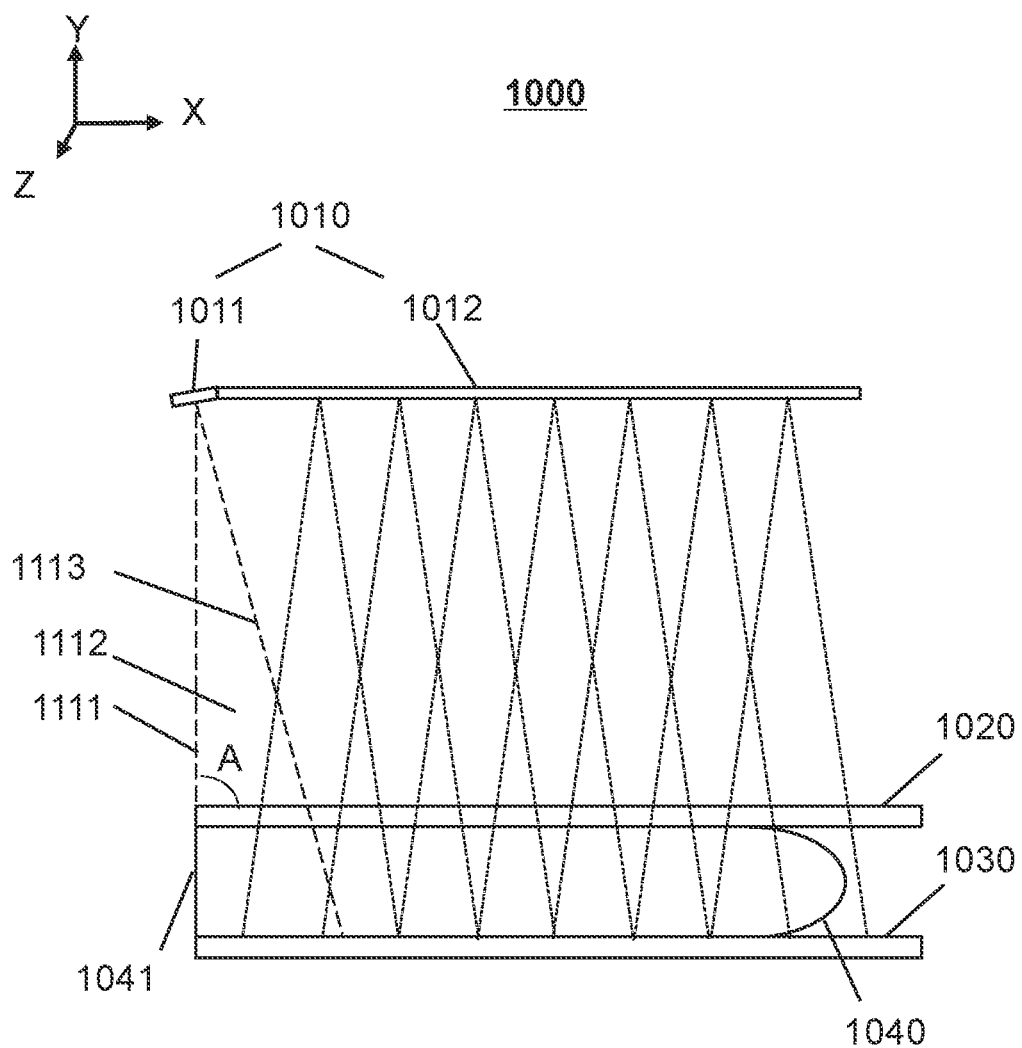
FIGS. 10 and 11 are schematic diagrams illustrating an exemplary medical device according to some embodiments of the present disclosure.
Figure 11:
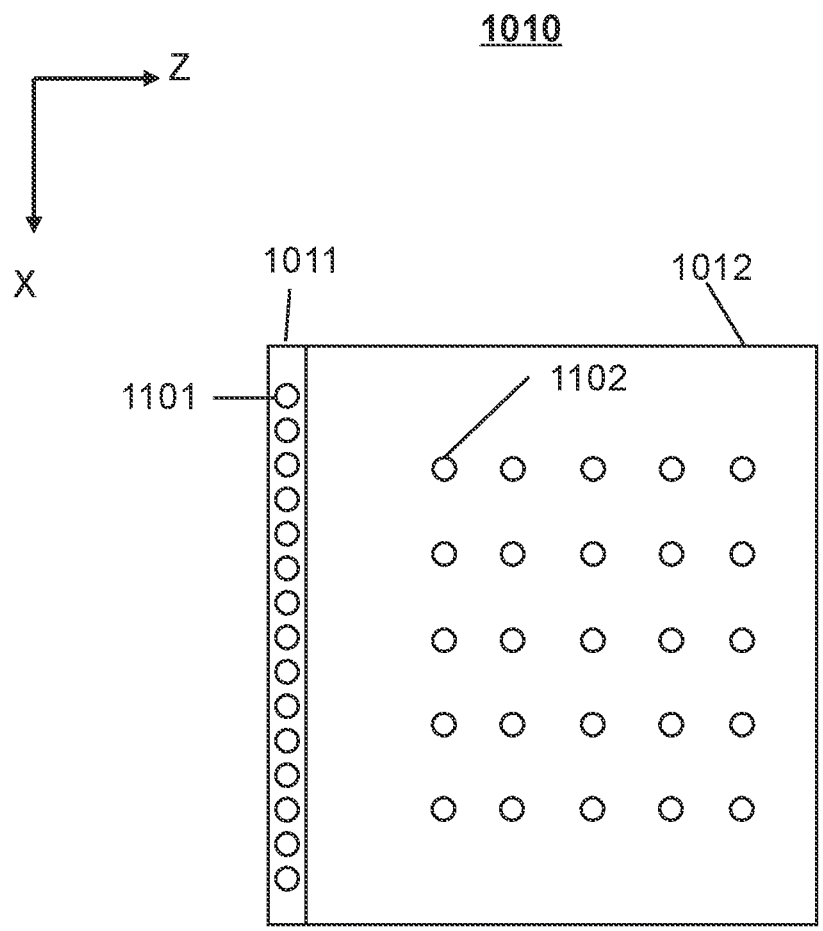

FIGS. 10-12 are schematic diagrams illustrating an exemplary medical device according to some embodiments of the present disclosure.

As illustrated in FIG. 10 (i.e., a side view of a medical device 1000), the medical device 1000 may include an array radiation source 1010, a compression component 1020, and a detector 1030. The compression component 1020 may be located between the array radiation source 1010 and the detector 1030. The compression component 1020 may be configured to position a breast 1040 of a patient. The detector 1030 may be similar to the detector 112 as described in connection with FIG. 1. The compression component 1020 may be similar to the compression component 114 as described in connection with FIG. 1. The array radiation source 1010 may include a linear array radiation source 1011 and a planar array radiation source 1012. The linear array radiation source 1011 may be configured on a chest-wall side 1041 of the breast 1040. As used herein, a chest-wall side of a breast refers to a side of the breast away from the nipple of the breast.

In some embodiments, as illustrated in FIG. 11 (i.e., a top view of the array radiation source 1010), the linear array radiation source 1011 may include a plurality of first point radiation sources 1101, and the planar array radiation source 1012 may include a plurality of second point radiation sources 1102. The plurality of first point radiation sources 1101 may be arranged along a straight line. The plurality of second point radiation sources 1102 may form an array of 5×5 (5 columns by 5 rows) second point radiation sources. Since most breast diseases occur on the chest-wall side 1041 of the breast 1040, that is, a portion of the breast 1040 on the chest-wall side 1041 is more likely to have a lesion than other portions of the breast 1040. In order to improve the quality of a reconstructed image of the portion of the breast 1040 on the chest-wall side 1041, a signal-to-noise ratio of the array radiation source 1010 corresponding to the chest-wall side 1041 of the breast 1040 may need to increase. As used herein, a signal-to-noise ratio refers to a ratio of the level of a desired signal to the level of noise, or a ratio of variances of the signal and the noise. Compared to a relatively low signal-to-noise ratio, a relatively high signal-to-noise ratio may correspond to a relatively high quality of a reconstructed image. In some embodiments, the signal-to-noise ratio of the array radiation source 1010 may correlate with a power of the array radiation source 1010. For example, a first power of the linear array radiation source 1011 may be greater than a second power of the planar array radiation source 1012.

In some embodiments, the signal-to-noise ratio of the array radiation source 1010 may be associated with an arrangement density of a plurality of point radiation sources of the array radiation source 1010. As used herein, an arrangement density refers to a number (or count) of point radiation sources in a unit area of an array radiation source. For example, a relatively high arrangement density of the plurality of point radiation sources of the array radiation source 1010 may correspond to a relatively high signal-to-noise ratio of the array radiation source 1010. In some embodiments, an arrangement density of the plurality of first point radiation sources 1101 of the linear array radiation source 1011 may be higher than an arrangement density of the plurality of second point radiation sources 1102 of the planar array radiation source 1012, as illustrated in FIG. 11. For example, a first distance between adjacent first point radiation sources 1101 of the linear array radiation source 1011 may be the same, a second distance between adjacent second point radiation sources 1102 of the planar array radiation source 1012 may be the same, and the first distance may be less than the second distance.

In some embodiments, the first power of the linear array radiation source 1011 may be equal to the second power of the planar array radiation source 1012, and the arrangement density of the plurality of first point radiation sources 1101 of the linear array radiation source 1011 may be higher than the arrangement density of the plurality of second point radiation sources 1102 of the planar array radiation source 1012. In some embodiments, the arrangement density of the plurality of first point radiation sources 1101 of the linear array radiation source 1011 may be equal to the arrangement density of the plurality of second point radiation sources 1102 of the planar array radiation source 1012, and the first power of the linear array radiation source 1011 may be higher than the second power than the planar array radiation source 1012.

In some embodiments, a plurality of first radiation beams emitted by the plurality of first point radiation sources 1101 of the linear array radiation source 1011 may form a radiation region 1112. The radiation region 1112 may be of a cone shape, a quadrangular pyramid shape, a prism shape, or the like. In some embodiments, the radiation region 1112 may include a first radiation surface 1111 and a second radiation surface 1113. The first radiation surface 1111 and the second radiation surface 1113 may define the boundary of the radiation region 1112 along the X-axis direction as illustrated in FIG. 10. The first radiation surface 1111 may be closer to the chest-wall side 1041 of the breast 1040 than the second radiation surface 1113. In some embodiments, the first radiation surface 1111 in the radiation region 1112 may be (substantially) parallel to the chest-wall side 1041 of the breast 1040. That is, the first radiation surface 1111 in the radiation region 1112 may be (substantially) perpendicular to the compression component 1020. Accordingly, the plurality of first radiation beams emitted by the plurality of first point radiation sources 1101 of the linear array radiation source 1011 may not traverse the chest-wall side 1041 of the breast 1040, which may avoid or reduce the undesired or unnecessary radiation to a patient. As used herein, a first surface being substantially perpendicular to a second surface indicates that the deviation of the angle between the first surface and the second surface from a right angle is below a threshold. Merely by way of example, the first surface being substantially perpendicular to the second surface indicates that the angle between the first surface and the second surface is in the range of 89°~91°, 88°~92°, 85°~95°, or the like.

Figure 12A:
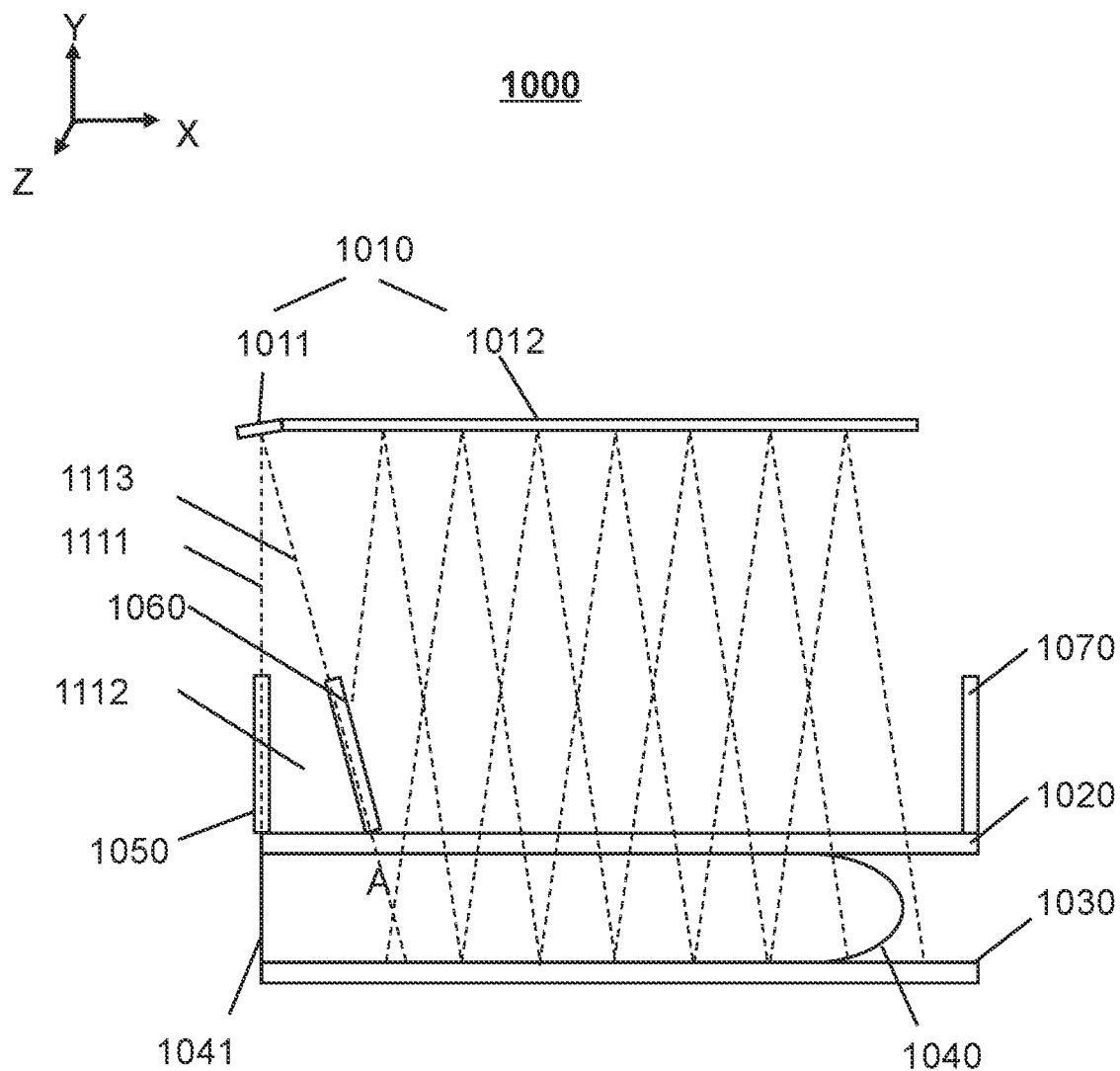
FIGS. 12A, 12B, and 12C are schematic diagrams illustrating an exemplary medical device according to some embodiments of the present disclosure.

In some embodiments, as illustrated in FIG. 12A, the medical device 1000 may include one or more shielding components (e.g., a first shielding component 1060, a second shielding component 1050, a third shielding component 1070). In some embodiments, when the linear array radiation source 1011 and the planar array radiation source 1012 emit radiation beams simultaneously, a plurality of first radiation beams emitted by the plurality of first point radiation sources 1101 of the linear array radiation source 1011, and a plurality of second radiation beams emitted by the plurality of second point radiation sources 1102 of the planar array radiation source 1012 may partially overlap, and the breast 1040 may be subject to unnecessary radiation. The first shielding component 1060 may be configured to prevent a radiation beam emitted by the planar array radiation source 1012 from traversing the radiation region 1112 formed by the linear array radiation source 1011. The first shielding component 1060 may be (substantially) parallel to the second radiation surface 1113 in the radiation region 1112.

In some embodiments, the first shielding component 1060 may be configured on the compression component 1020. The first shielding component 1060 may be fixedly or moveably configured on the compression component 1020 via a chemical component (e.g., an adhesive), a fastener (e.g., a nail, a screw, a nut), a snap, or the like, or any combination thereof. For example, two ends of the first shielding component 1060 contacting the compression component 1020 or in proximity to the compression component 1020 (compared to the ends of the first shielding component 1060 closer to the array radiation source 1010) may be fixedly or moveably attached on two ends of the compression component 1020, respectively. In this situation, the first shielding component 1060 may be in contact with the compression component 1020, or may not be in contact with the compression component 1020.

The second shielding component 1050 may be configured to prevent a radiation beam emitted by the planar array radiation source 1012 and/or the linear array radiation source 1011 from traversing or irradiating the chest-wall side 1041 of the breast 1040. The second shielding component 1050 may be (substantially) parallel to the chest-wall side 1041 of the breast 1040. That is, the second shielding component 1050 may be (substantially) perpendicular to the compression component 1020. In some embodiments, the second shielding component 1050 may be fixedly or moveably configured on the compression component 1020. For example, the second shielding component 1050 may be configured on an end of the compression component 1020 closest to the chest-wall side 1041 of the breast 1040. As another example, the second shielding component 1050 may be configured on an upper surface of compression component 1020. As used herein, an upper surface of the compression component 1020 refers to a surface of the compression component 1020 that is close to the array radiation source 1010 and away from the detector 1030.

The third shielding components 1070 may be configured to prevent a radiation beam emitted by the planar array radiation source 1012 and/or the linear array radiation source 1011 from traversing or irradiating a region (e.g., an arm, the abdomen) other than the breast 1040 of the patient, and/or a user (e.g., a doctor) of the medical device 1000. The third shielding component 1070 may be fixedly or moveably configured on a side perpendicular to the chest-wall side 1041 of the breast 1040 (not shown in FIG. 12A), and/or a side opposite to the chest-wall side 1041 of the breast 1040, as illustrated in FIG. 12A. In some embodiments, the third shielding component 1070 may be configured on the compression component 1020. For example, the third shielding component 1070 may be configured on an end of the compression component 1020 away from the chest-wall side

1041 of the breast 1040, as illustrated in FIG. 12. As another example, the third shielding component 1070 may be configured on an end of the compression component 1020 perpendicular to the chest-wall side 1041 of the breast 1040.

In some embodiments, the first shielding component 1060, the second shielding component 1050, and/or the third shielding component 1070 may be made of a high atomic number material (e.g., a material containing lead or iron). For example, the first shielding component 1060, the second shielding component 1050, and/or the third shielding component 1070 may be made of lead rubber, radiation-proof inorganic lead glass, radiation-proof organic lead glass, glass steel composite protective material, or the like. In some embodiments, the first shielding component 1060, the second shielding component 1050, and/or the third shielding component 1070 may have any suitable shape and any suitable size, such that the first shielding component 1060, the second shielding component 1050, and/or the third shielding component 1070 can prevent a radiation beam emitted by the planar array radiation source 1012 and/or the linear array radiation source 1011 from traversing a corresponding region of the breast 1040 of the patient, or a user (e.g., a doctor) of the medical device 1000. For example, the first shielding component 1060, the second shielding component 1050, and/or the third shielding component 1070 may be a rectangular plate, a square plate, a circular plate, or the like. In some embodiments, the materials, sizes, and/or shapes of the first shielding component 1060, the second shielding component 1050, and the third shielding component 1070 may be the same or different.

In some embodiments, the medical device 1000 may include a first driving device (not shown in FIG. 12A) configured to drive the first shielding component 1060 to move (e.g., translate, rotate) relative to the compression component 1020. For example, the first driving device may adjust a position of the first shielding component 1060 relative to the compression component 1020, and an inclination angle of the first shielding component 1060 relative to the compression component 1020. In some embodiments, the first driving device may include a first power component and a first driving component. The first power component may be connected to the first driving component, and the first driving component may move driven by the first power component to drive the first shielding component 1060 to move relative to the compression component 1020. In some embodiments, the first power component may include a motor. The first driving component may include a wire drive mechanism, a hinge driving mechanism, a gear and rack driving mechanism, a screw and nut driving mechanism, or the like. Merely by way of example, the first driving component may include one or more telescopic rods hingedly connected with the first shielding component 1060. The position and the inclination angle of the first shielding component 1060 may be adjusted by controlling the extension length of the one or more telescopic rods.

In some embodiments, the medical device 1000 may include a second driving device (not shown in FIG. 12A) configured to drive the detector 1030 to move relative to the array radiation source 1010. In some embodiments, the second driving device may include a second power component and a second driving component. The second power component may be connected to the second driving component, and the second driving component may move driven by the second power component to drive the detector 1030 to move relative to the array radiation source 1010. For example, the second power component may include a motor, and the second driving component may include one or more telescopic rods connected with the detector 1030.

In some embodiments, the medical device 1000 may include a third driving device (not shown in FIG. 12A) configured to drive the compression component 1020 to position (e.g., compresses) the breast 1040. In some embodiments, the third driving device may include a third power component and a third driving component. The third power component may be connected to the third driving component, and the third driving component may move driven by the third power component to drive the compression component 1020 to compresses the breast 1040. For example, the third power component may include a motor, and the third driving component may include one or more telescopic rods connected with the compression component 1020.

In some embodiments, a fixed SID scan may be performed on the breast 1040 by the medical device 1000. As used herein, a fixed SID scan refers that the SID is fixed when the scan is performed on a subject. In some embodiments, the SID may be selected or specified by a user (e.g., a doctor) of the medical system 100, or determined by one or more components (e.g., the processing device 120) of the medical system 100 according to different situations. During a fixed SID scan, the position of the array radiation source 1010 and the position of the detector 1030 are fixed; when the compression component 1020 positions (e.g., compresses) the breast 1040, the thickness of the breast 1040 along the Y-axis direction may change compared to when the compression component 1020 is not pressed on the breast 1040, and a distance between the array radiation source 1010 and the compression component 1020 may change compared to when the compression component 1020 is not pressed on the breast 1040. A position of the first shielding component 1060 configured on the compression component 1020 relative to the radiation region 1112 may change, which may change the amount of radiation irradiating the breast 1040, and may further affect the quality of a reconstructed image of the breast 1040.

Figure 12B:
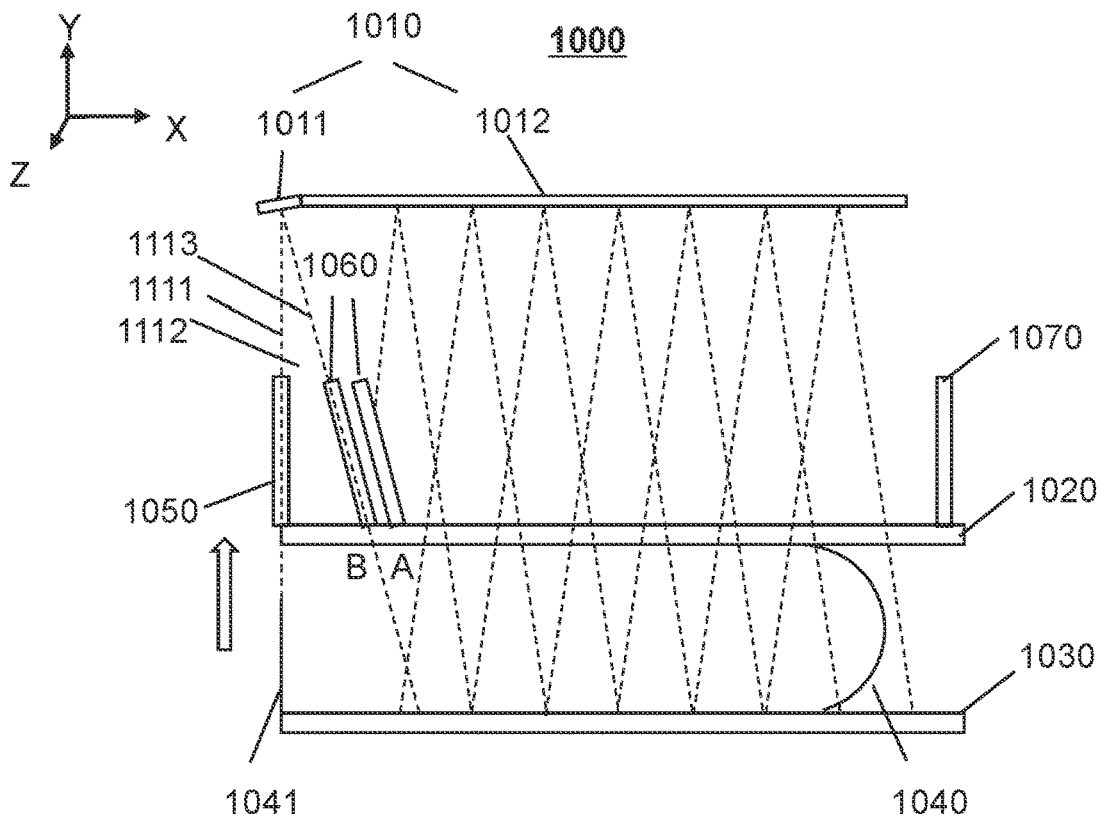

For example, if the compression component 1020 moves upward along the positive Y-axis direction as illustrated in FIG. 12B, the first shielding component 1060 configured on the compression component 1020 at a position A may block the radiation beams emitted by the planar array radiation source 1012, and a region of the breast 1040 may not receive the radiation beams emitted by the linear array radiation source 1011 and the planar array radiation source 1012. The first shielding component 1060 may need to move from the position A to a position B on the compression component 1020 to substantially coincide with the second radiation surface 1113 of the radiation region 1112 formed by the linear array radiation source 1011.

Figure 12C:
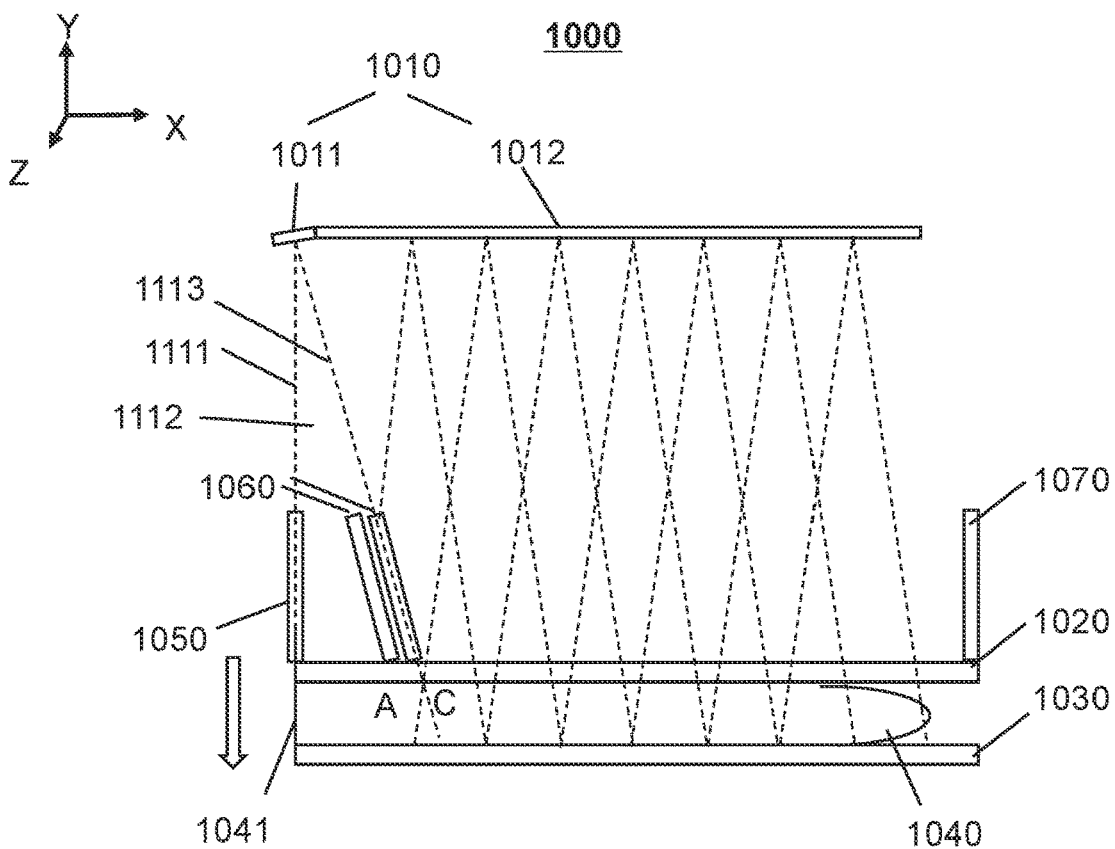

Similarly, if the compression component 1020 moves downward along the negative Y-axis direction as illustrated in FIG. 12C, the first shielding component 1060 configured on the compression component 1020 at the position A may block at least part of the radiation beams emitted by the linear array radiation source 1011, and a region of the breast 1040 may not receive the radiation beams emitted by the linear array radiation source 1011 and the planar array radiation source 1012. The first shielding component 1060 may need to move from the position A to a position C on the compression component 1020 to substantially coincide with the second radiation surface 1113 of the radiation region 1112 formed by the linear array radiation source 1011.

In some embodiments, during the fixed SID scan, the movement of the compression component 1020 and the movement of the first shielding component 1060 on the compression component 1020 may be performed simultaneously. Alternatively, after the compression component 1020 positions the breast 1040, the position of the first shielding component 1060 on the compression component 1020 may be adjusted. The extent to which the first shielding component 1060 needs to move may be determined based on the moving distance and the moving direction of the compression component 1020.

In some embodiments, a fixed SOD scan may be performed on the breast 1040 by the medical device 1000. As used herein, a fixed SOD scan refers that the SOD is fixed when the scan is performed on a subject. In some embodiments, the SOD may be manually set by a user (e.g., a doctor) of the medical system 100, or determined by one or more components (e.g., the processing device 120) of the medical system 100 according to different situations. In some embodiments, during the fixed SOD scan, the position of the detector 1030 may be fixed, when the compression component 1020 positions (e.g., compresses) the breast 1040, the thickness of the breast 1040 along the Y-axis direction may change, and the position of the array radiation source 1010 may be adjusted to keep the SOD fixed. Alternatively, during the fixed SOD scan, the positions of the array radiation source 1010 and the compression component 1020 may be fixed, and the position of the detector 1030 may be adjusted to position the breast 1040.

According to some embodiments of the present disclosure, during the scan of the breast 1040 by the medical device 1000, a plurality of point radiation sources of an array radiation source 1010 (e.g., the linear array radiation source 1011, the planar array radiation source 1012) of the medical device 1000 may emit a plurality of radiation beams to the breast 1410 from different directions when the position of the array radiation source 1010 is fixed (i.e., without rotating around the breast 1410). Therefore, the effective focal spot size of the array radiation source 1010 may be reduced, and the quality of a reconstructed image of the breast 1410 may be improved. The scanning time may be reduced, the probability and/or extent of movement of the subject during the scan may be reduced, and a motion blur in the reconstructed image caused by the movement of the breast 1410 may be avoided or reduce.

In addition, the arrangement density of the plurality of first point radiation sources 1101 of the linear array radiation source 1011 may be higher than the arrangement density of the plurality of second point radiation sources 1102 of the planar array radiation source 1012, which may improve the quality of the reconstructed image of the portion of the breast 1040 on the chest-wall side 1041. Furthermore, the one or more shielding components (e.g., the first shielding component 1060, the second shielding component 1050, the third shielding component 1070) in the medical device 1000 may prevent the patient and/or the user (e.g., the doctor) of the medical device 1000 from receiving unnecessary radiation.

It should be noted that the above descriptions merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the first power component, the second power component, and the third power component may be integrated into a single power component. In some embodiments, the medical device 1000 may include a control device configured to control the one or more components (e.g., the array radiation source 1010, the compression component 1020, the detector 1030, the one or more shielding components, the one or more driving devices) of the medical device 1000. The control device may be connected to and/or communicate with the one or more components of the medical device 1000. For example, the control device may determine at least one parameter of the array radiation source 1010. As another example, the control device may control the first driving device to drive the first shielding component 1060 to move relative to the compression component 1020. As another example, the control device may control the second driving device to drive the detector 1030 to move relative to the at least one array radiation source 1010. As another example, the control device may control the third driving device to drive the compression component 1020 to position the breast 1040. As another example, the control device may control the detector 1030 to detect radiation beams that have crossed the breast 1040. As another example, the control device may generate a breast image by processing the detected radiation beams. In some embodiments, the control device may control the one or more components of the medical device 1000 automatically or according to a user instruction.

Figure 13:
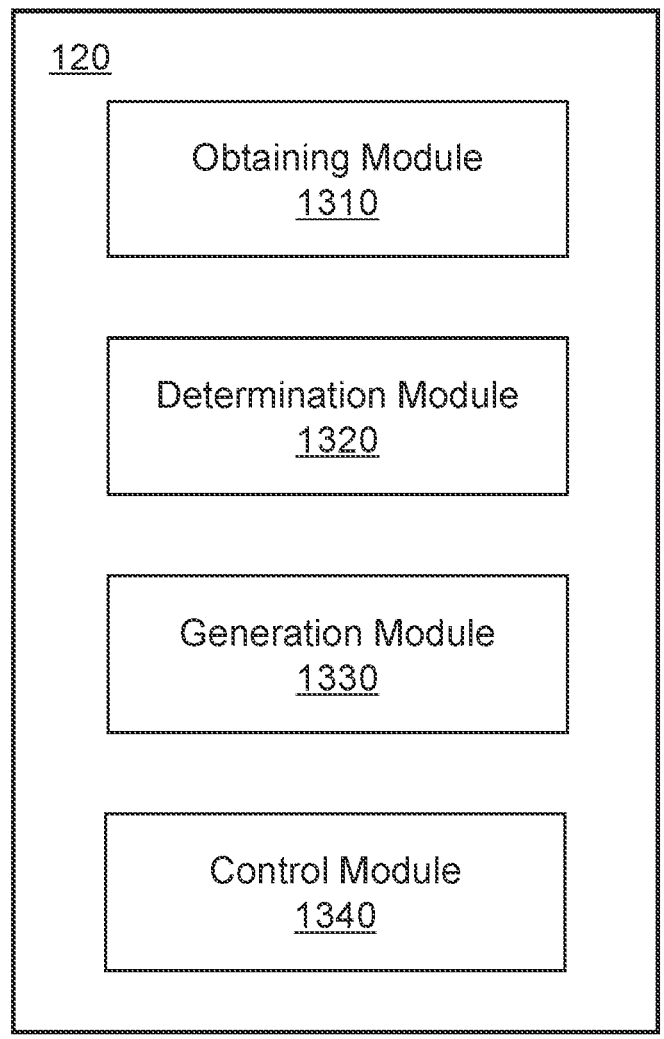
FIG. 13 is a block diagram illustrating an exemplary processing device according to some embodiments of the present disclosure.

FIG. 13 is a block diagram illustrating an exemplary processing device according to some embodiments of the present disclosure. In some embodiments, the processing device 120 may include an obtaining module 1310, a determination module 1320, a generation module 1330, and a control module 1340.

The obtaining module 1310 may be configured to obtain data and/or information associated with the medical system 100. The data and/or information associated with the imaging system 100 may include information of a subject, at least one parameter of an array radiation source of a medical device, an energy of a detected X-ray photon, or the like, or any combination thereof. For example, the obtaining module 1310 may obtain at least one parameter of an array radiation source of a medical device based on information of a subject (e.g., a patient) to be scanned by the medical device. As another example, the obtaining module 1310 may obtain energies of detected X-ray photons corresponding to a radiation beam emitted by a point radiation source, and a count of detected X-ray photons corresponding to the radiation beam. In some embodiments, the obtaining module 1310 may obtain the data and/or the information associated with the medical system 100 from one or more components (e.g., the terminal 140, the storage device 130, the medical device 110) of the medical system 100 via the network 150.

The determination module 1320 may be configured to determine a candidate image corresponding to a point radiation source of a medical device. In some embodiments, the determination module 1320 may determine a candidate image corresponding to a point radiation source based on an energy range of a radiation beam emitted by the point radiation source, energies of detected X-ray photons corresponding to the radiation beam, and a count of the detected X-ray photons corresponding to the radiation beam. For example, for each detected X-ray photon, the determination module 1320 may obtain an energy of the detected X-ray photon. The determination module 1320 may determine a specific point radiation source corresponding to the detected X-ray photon based on the energy of the detected X-ray photon and an energy range of a radiation beam emitted by each point radiation source of a plurality of point radiation source. The determination module 1320 may determine a count of detected X-ray photons corresponding to the each point radiation source. The determination module 1320 may determine the candidate image corresponding to the each point radiation source based on the count of detected X-ray photons corresponding to the each point radiation source, and the energies of detected X-ray photons corresponding to the each point radiation source. More descriptions of the determination of the candidate image may be found elsewhere in the present disclosure (e.g., FIG. 15, and descriptions thereof).

The generation module 1330 may be configured to generate an image of a subject based on a scan. In some embodiments, the generation module 1330 may generate a target image based on a plurality of candidate images corresponding to a plurality of point radiation sources of a medical device. For example, the generation module 1330 may generate a target image based on a plurality of candidate images corresponding to a plurality of point radiation sources and a plurality of radiation angles corresponding to the plurality of point radiation sources according to one or more reconstruction algorithms. More descriptions of the determination of the target image may be found elsewhere in the present disclosure (e.g., FIG. 15, and descriptions thereof).

The control module 1340 may be configured to control one or more components (e.g., the medical device 110, the terminal 140) of the medical system 100. For example, the control module 1340 may cause a medical device to perform a scan on a subject based on at least one parameter of at least one array radiation source. As another example, the control module 1340 may cause each point radiation source of at least some of a plurality of point radiation sources of an array radiation source to simultaneously emit a radiation beam to a subject.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the determination module 1320 and the generation module 1330 may be combined into a single module. In some embodiments, one or more modules may be added or omitted in the processing device 120. For example, the processing device 120 may further include a storage module (not shown in FIG. 13) configured to store data and/or information (e.g., information of the subject, at least one parameter of at least one array radiation source of a medical device, an image of the subject) associated with the medical system 100.

Figure 14:
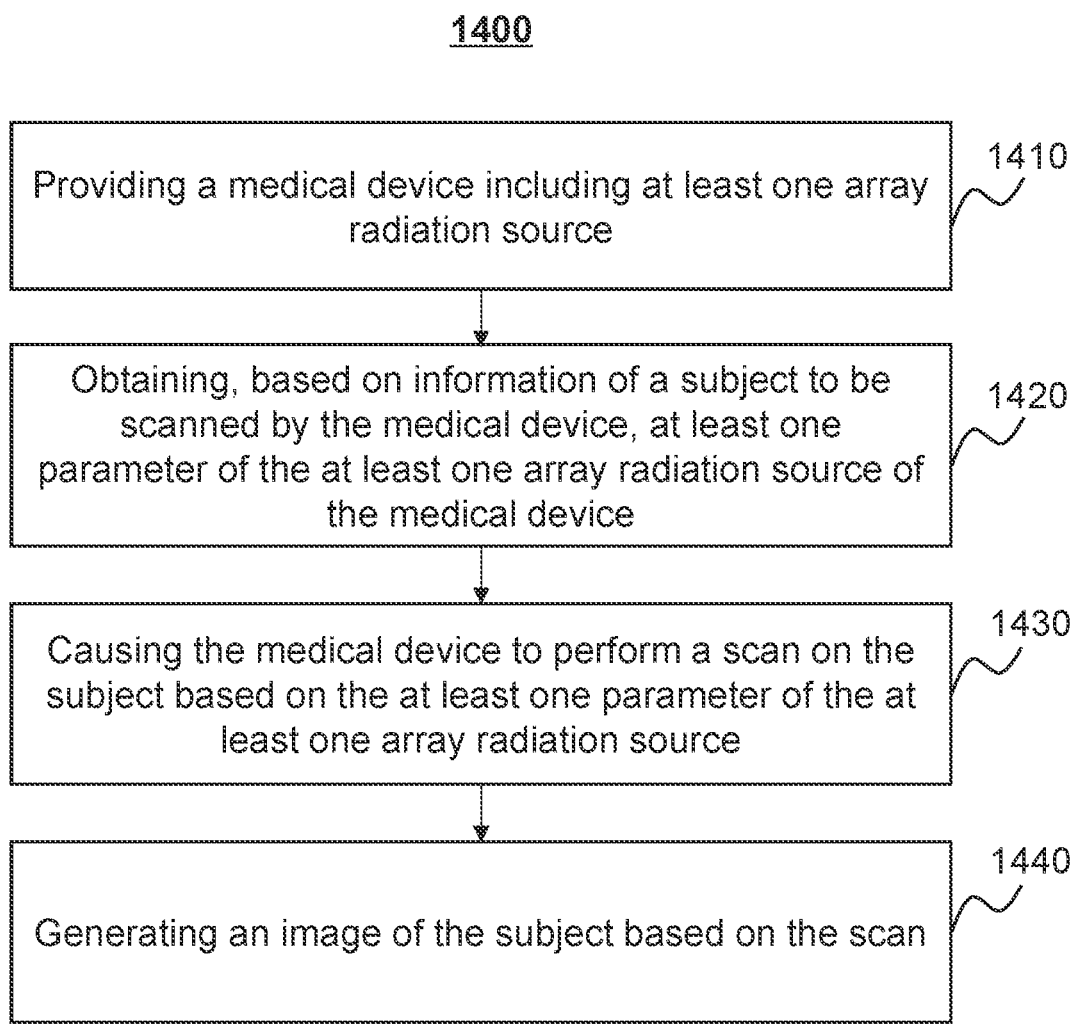
FIG. 14 is a flowchart illustrating an exemplary process for generating an image according to some embodiments of the present disclosure.

FIG. 14 is a flowchart illustrating an exemplary process for generating an image of a subject according to some embodiments of the present disclosure. In some embodiments, the process 1400 may be implemented in the medical system 100 illustrated in FIG. 1. For example, the process 1400 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3, one or more modules as shown in FIG. 13). The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1410, a medical device (e.g., the medical device 110, the medical device 500, the medical device 600, the medical device 900, the medical device 1000) including at least one array radiation source (e.g., the linear array radiation source 518, the planar array radiation source 618, the array radiation source 800, the array radiation source 910, the array radiation source 1010) may be provided. More descriptions of the medical device and the array radiation source may be found elsewhere in the present disclosure (e.g., FIGS. 1 and 5-12C, and descriptions thereof).

In 1420, the processing device 120 (e.g., the obtaining module 1310) may obtain, based on information of a subject (e.g., a patient) to be scanned by the medical device, at least one parameter of the at least one array radiation source of the medical device.

In some embodiments, the at least one parameter of the at least one array radiation source may include a position of the at least one array radiation source, a position of at least one of a plurality of point radiation sources of the at least one array radiation source, an orientation of the at least one of the plurality of point radiation sources, a radiation dose of the at least one radiation beam, an energy range of a radiation beam emitted from the at least one of the plurality of point radiation sources, a radiation time of the at least one of the plurality of point radiation sources, a radiation sequence of the plurality of point radiation sources, or the like, or any combination thereof.

The position of the at least one array radiation source may include a position of the at least one array radiation source relative to a gantry of the medical device, a position of at least one radiation source panel of the at least one array radiation source, an angle between two radiation source panels of the at least one array radiation source, or the like, or any combination thereof. The position of the at least one of the plurality of point radiation sources may include a position of a point radiation source that emit a radiation beam when a scan is performed on the subject, or the like. For example, referring to FIG. 7, point radiation sources F1, F2, F3, E1, E2, E3, D1, D2, D3 of the planar array radiation source 618 may emit radiation beams and other point radiation sources of the planar array radiation source 618 may not emit radiation beams when a scan is performed on the subject 113. As used herein, a radiation time of a point radiation source refers to a duration the point radiation source emits a radiation beam. As used herein, the radiation sequence of the plurality of point radiation sources refers to a sequence in which the plurality of point radiation sources emit radiation beams. For example, the plurality of point radiation sources may emit the radiation beams simultaneously. As another example, the plurality of point radiation sources may emit the radiation beams one by one according to a rule.

The information of the subject may include feature information (e.g., a height, a width, a thickness, a weight, the gender, the age) of the subject, a health condition, historical scan information, a scan area of the subject, or the like, or any combination thereof. As used herein, a width of a subject refers to a length of the subject (e.g., a length at the center of the subject, a maximum length of the subject) along a direction perpendicular to a sagittal plane of the subject. A height of a subject refers to a length of the subject (e.g., a length at the center of the subject, a maximum length of the subject) along a direction perpendicular to a transverse plane of the subject. As used herein, a scan area of a subject refers to a region of the subject to be scanned by a medical device. For example, the scan area may be a breast of a patient. In some embodiments, the information of the subject may be previously collected and stored in a storage device (e.g., the storage device 130, the storage 220, the storage 390, or an external source). The processing device 120 may retrieve the information of the subject from the storage device. In some embodiments, a user (e.g., a doctor) of the medical system 100 may manually input the information of the subject via a terminal device (e.g., the terminal 140) of the user.

In some embodiments, the processing device 120 may determine the at least one parameter of the at least one array radiation source of the medical device based on the information of the subject and a relationship between the information of the subject and the at least one parameter of the at least one array radiation source. For example, the relationship may be represented in the form of a table recording different information of the subject and their corresponding value(s) of the parameter(s) of the at least one array radiation source. The relationship between the information of the subject and the parameter(s) of the at least one array radiation source may be stored in a storage device, and the processing device 120 may retrieve the relationship from the storage device. In some embodiments, the relationship between the information of the subject and the parameter(s) of the at least one array radiation source may be determined by the processing device 120 based on experimental data. For example, a relationship between the breast of the subject and the parameter(s) of the at least one array radiation source may be obtained or determined by performing a plurality of simulation scans on the breast of the subject. In some embodiments, the relationship may be subject-specific; that is, the relationship is applicable only to the subject. In some embodiments, the relationship may be group specific; that is the relationship is applicable to a group of subjects who share one or more features or characteristics. Exemplary features or characteristics may include the gender of a subject, the build or body type of a subject, the bust of a subject, the body mass index (BMI) of a subject, a suspected health condition of a subject, a medical history of a subject, the age of a subject, or the like, or a combination thereof.

In some embodiments, the processing device 120 may obtain a scan protocol of the subject based on the information of the subject. The scan protocol may include, for example, value(s) or value range(s) of scan parameter(s) (e.g., parameter(s) of array radiation source(s)), an SID, an SOD, a scan area of the subject, feature information of the subject (e.g., the gender, the weight, the age), or the like, or any combination thereof. For example, if the scan area of the subject is the breast and the body shape of the subject is medium, a scan protocol corresponding to a breast examination and a medium body shape may be obtained. Further, the processing device 120 may determine the at least one parameter of the at least one array radiation source based on the scan protocol of the subject. The scan protocol may be previously generated (e.g., manually input by a user or determined by the processing device 120) and stored in a storage device. The processing device 120 may retrieve the scan protocol from the storage device, and determine the at least one parameter of the at least one array radiation source based on the scan protocol.

In 1430, the processing device 120 (e.g., the control module 1340) may cause the medical device to perform a scan on the subject based on the at least one parameter of the at least one array radiation source.

In some embodiments, the processing device 120 may send instructions to operate the medical device to adjust parameter(s) and/or position(s) of component(s) (e.g., the array radiation source, a detector, a compression component, a holder) of the medical device. Further, the processing device 120 may cause the medical device to perform the scan on the subject. For example, the processing device 120 may determine a position of the detector based on a position of the array radiation source and the SID in the scan protocol of the subject. As another example, the processing device 120 may control a state (e.g., whether to emit a radiation beam) of a specific point radiation source of the array radiation source by controlling a state of an electromagnetic coil (e.g., the electromagnetic coil 830 illustrated in FIG. 8) corresponding to the specific point radiation source. As another example, the processing device 120 may control a radiation dose and/or an energy range of a radiation beam emitted by a specific point radiation source of the array radiation source by controlling a power of the specific point radiation source. In some embodiments, the medical device may include an adjustment device configured to adjust the power of at least one point radiation source of the plurality of point radiation sources of the array radiation source. The processing device 120 may control the adjustment device to adjust the power of the at least one point radiation source of the plurality of point radiation sources of the array radiation source. In some embodiments, one adjustment device may correspond to one or more point radiation sources.

In 1440, the processing device 120 (e.g., the generation module 1330) may generate an image of the subject based on the scan.

In some embodiments, each point radiation source of the plurality of point radiation sources may emit a radiation beam at a corresponding radiation angle. The detector may detect the radiation beam, and generate data associated with the projection formed by the detected radiation beams (e.g., X-rays beams) as image data (also referred to as projection data) corresponding to the each point radiation source. The processing device 120 may then generate the image of the subject based on image data corresponding to the plurality of point radiation sources and radiation angles of the plurality of point radiation sources according to one or more reconstruction algorithms. The one or more reconstruction algorithms may include an iterative reconstruction algorithm (e.g., a statistical reconstruction algorithm), a Fourier slice theorem algorithm, a fan-beam reconstruction algorithm, an analytic reconstruction algorithm (e.g., a filtered back projection (FBP) algorithm), an algebraic reconstruction technique (ART), a simultaneous algebra reconstruction technique (SART), a Feldkamp-Davis-Kress (FDK) reconstruction technique, or the like, or any combination thereof.

It should be noted that the above description regarding process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the at least one parameter of the at least one array radiation source of the medical device may be manually set by a user (e.g., a doctor) of the medical system 100 based on user experience. As another example, after the at least one parameter of the at least one array radiation source is determined by the processing device 120, the user may further adjust the at least one parameter of the at least one array radiation source.

In some embodiments, the processing device 120 may determine the at least one parameter of the at least one array radiation source based on the information of the subject using a parameter determination model. The parameter determination model refers to a model (e.g., a machine learning model) or an algorithm for determining parameter(s) of an array radiation source based on information of a subject. For example, the processing device 120 may input the information of the subject into the parameter determination model, and the parameter determination model may output the parameter(s) of the array radiation source by processing the information of the subject.

FIG. 15 is a flowchart illustrating an exemplary process for generating a target image of a subject according to some embodiments of the present disclosure. In some embodiments, the process 1500 may be implemented in the medical system 100 illustrated in FIG. 1. For example, the process 1500 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3, one or more modules as shown in FIG. 13). The operations of the illustrated process presented below are intended to be illustrative. In some embodiments, the process 1500 may be accomplished with one or more additional operations not described, and/or without one or more of the operations discussed. Additionally, the order in which the operations of the process 1500 as illustrated in FIG. 15 and described below is not intended to be limiting.

In 1510, the processing device 120 (e.g., the control module 1340) may cause each point radiation source of at least some of a plurality of point radiation sources (e.g., the point radiation source 520 illustrated in FIG. 5, the point radiation source A1, A2, . . . X1, X2 illustrated in FIG. 6) of an array radiation source (e.g., the linear array radiation source 518, the planar array radiation source 618, the array radiation source 800, the array radiation source 910, the array radiation source 1010) to simultaneously emit a radiation beam to a subject (e.g., a breast). The subject may be located between the array radiation source and a detector (e.g., the detector 112, the detector 920, the detector 1030). In some embodiments, each radiation beam may include a plurality of X-ray photons. At least two radiation beams emitted by the plurality of point radiation sources may be different. In some embodiments, the at least two radiation beams emitted by the plurality of point radiation sources may be of different energy ranges as described in FIGS. 6 and 7. For example, a plurality of energy ranges of a plurality of radiation beams emitted by the plurality of point radiation sources may partially overlap. As another example, the plurality of energy ranges of the plurality of radiation beams emitted by the plurality of point radiation sources may not overlap.

In 1520, for each of the plurality of point radiation sources, the processing device 120 (e.g., the obtaining module 1310) may obtain energies of detected X-ray photons corresponding to the radiation beam emitted by the each point radiation source and a count of the detected X-ray photons corresponding to the radiation beam from the detector. In some embodiments, the detector may be a photon counting detector. The photon counting detector may detect an energy of a detected X-ray photon, and count the detected X-ray photons of different energy ranges.

In 1530, for each of the plurality of point radiation sources, the processing device 120 (e.g., the determination module 1320) may determine a candidate image corresponding to the each point radiation source based on an energy range of the radiation beam emitted by the each point radiation source, the energies of the detected X-ray photons corresponding to the radiation beam, and the count of detected X-ray photons corresponding to the radiation beam.

As used herein, a candidate image corresponding to a specific point radiation source refers that the candidate image is generated based on a radiation beam (e.g., a plurality of X-ray photons) emitted from the specific point radiation source. For example, the specific point radiation source may emit a radiation beam at a corresponding radiation angle. The detector may detect the radiation beam, and generate data associated with the projection formed by the detected radiation beams (e.g., X-rays beams) as the candidate image (also referred to as projection data) corresponding to the specific point radiation source.

In some embodiments, for each detected X-ray photon, the processing device 120 may obtain the energy of the detected X-ray photon. The processing device 120 may determine a specific point radiation source corresponding to the detected X-ray photon based on the energy of the detected X-ray photon and the energy range of the radiation beam emitted by the each point radiation source of the plurality of point radiation source. As used herein, a point radiation source corresponding to a detected X-ray photon refers to the point radiation source by which the detected X-ray photon is emitted. Merely by way of example, assuming that the array radiation source includes a first point radiation source, a second point radiation source, and a third point radiation source, a first energy range of a first radiation beam emitted by the first point radiation source is 15~30 keV, a second energy range of a second radiation beam emitted by the second point radiation source is 40~55 keV, and a third energy range of a third radiation beam emitted by the third point radiation source is 65~80 eV, an energy of a specific detected X-ray photon is 50 keV, and the processing device 120 may determine that the specific detected X-ray photon is emitted from the second point radiation source.

The processing device 102 may then determine the count of detected X-ray photons corresponding to the each point radiation source. Merely by way of example, assuming that energies of a plurality of detected X-ray photons are 50 keV, 20 keV, 25 keV, 15 keV, 65 keV, 78 keV, 42 keV, respectively. The processing device 120 may determine the count of detected X-ray photons corresponding to the first point radiation source, the second point radiation source, and the third point radiation source are 3, 2, and 2, respectively. Further, the processing device 120 may determine the candidate image corresponding to the each point radiation source based on the count of detected X-ray photons corresponding to the each point radiation source, and the energies of detected X-ray photons corresponding to the each point radiation source.

In 1540, the processing device 120 (e.g., the generation module 1330) may generate a target image based on the candidate images corresponding to the plurality of point radiation sources.

In some embodiments, the processing device 120 may generate the target image based on the plurality of candidate images (e.g., the projection data) corresponding to the plurality of point radiation sources and a plurality of radiation angles corresponding to plurality of point radiation sources according to one or more reconstruction algorithms. The one or more reconstruction algorithms may include an iterative reconstruction algorithm (e.g., a statistical reconstruction algorithm), a Fourier slice theorem algorithm, a fan-beam reconstruction algorithm, an analytic reconstruction algorithm (e.g., a filtered back projection (FBP) algorithm), an algebraic reconstruction technique (ART), a simultaneous algebra reconstruction technique (SART), a Feldkamp-Davis-Kress (FDK) reconstruction technique, or the like, or any combination thereof.

According to some embodiments of the present disclosure, the array radiation source including the plurality of point radiation sources may be provided. Multiple (some or all) point radiation sources of the plurality of point radiation sources may emit the radiation beam to the subject simultaneously. The at least two radiation beams emitted by the plurality of point radiation sources may be of different energy ranges. Accordingly, the scan time may be reduced. In addition, the target image of the subject may be generated based on the plurality of candidate images corresponding to the plurality of point radiation sources, which may improve the quality of the target image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may determine the specific point radiation source corresponding to the detected X-ray photon based on the energy of the detected X-ray photon, the energy range of the radiation beam emitted by the each point radiation source of the plurality of point radiation source, a position relationship between the each point radiation source and the detector, a position of the detector that detects the X-ray photon, or the like.

In some embodiments, if the plurality of energy ranges of the plurality of radiation beams emitted by the plurality of point radiation sources partially overlap. The detected X-ray photon with an energy in an overlapping energy range may be ignored; that is, the detected X-ray photons with the energy in the overlapping energy range are not used for generating a candidate image generation. Alternatively, the detected X-ray photon with the energy in the overlapping energy range of a first energy range and a second energy range may be designated as being in the first energy range and/or the second energy range according to a preset ratio. For example, a half of the detected X-ray photons with energies in the overlapping energy range may be designated as being in the first energy range, and the other half of the detected X-ray photons with energies in the overlapping energy range may be designated as being in the second energy range.

Merely by way of example, assuming that the array radiation source includes a first point radiation source, a second point radiation source, and a third point radiation source, a first energy range of a first radiation beam emitted by the first point radiation source is 20~40 keV, a second energy range of a second radiation beam emitted by the second point radiation source is 30~55 keV, an energy of a first detected X-ray photon is 20 keV, an energy of a second detected X-ray photon is 36 keV, an energy of a third detected X-ray photon is 39 keV, an energy of a fourth detected X-ray photon is 50 keV, an energy of a fifth detected X-ray photon is 55 keV, the processing device 120 may determine that the first detected X-ray photon is in the first energy range, the fourth detected X-ray photon and the fifth detected X-ray photon are in the second energy range. The second detected X-ray photon and the third detected X-ray photon may be ignored. Alternatively, the processing device 120 may determine that the second detected X-ray photon is in the first energy range, and the third detected X-ray photon is in the second energy range.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. An imaging system, comprising:
   at least one array radiation source each of which includes a plurality of point radiation sources, the at least one array radiation source being configured to emit at least one radiation beam; and
   a detector configured to detect at least part of the at least one radiation beam;
   wherein the imaging system is a digital breast tomosynthesis (DBT) system.

2. The imaging system of claim 1, wherein
   the at least one array radiation source includes a planar array radiation source,
   the planar array radiation source includes at least one radiation source panel, and
   the plurality of point radiation sources are configured on the at least one radiation source panel.

3. The imaging system of claim 2, wherein the planar array radiation source includes two radiation source panels arranged at an angle, and the angle between the two radiation source panels is adjustable.

4. The imaging system of claim 3, wherein a range of the angle between the two radiation source panels is from 140° to 180°.

5. The imaging system of claim 1, further comprising:
   a control device configured to control the at least one array radiation source to move along a guide rail to adjust a distance between the at least one array radiation source and the detector, or adjust at least one parameter of the at least one array radiation source.

6. The imaging system of claim 5, wherein the at least one parameter of the at least one array radiation source includes at least one of:
   a position of the at least one array radiation source,
   a position of at least one of the plurality of point radiation sources,
   an orientation of the at least one of the plurality of point radiation sources, or
   a radiation dose of the at least one radiation beam.

7. The imaging system of claim 1, wherein at least two radiation beams emitted by the array radiation sources are of different energy ranges.

8. The imaging system of claim 1, wherein
   a plurality of energy ranges of a plurality of radiation beams emitted by the array radiation sources do not overlap, and
   an energy difference between consecutive energy ranges is not less than an energy resolution of the detector.

9. The imaging system of claim 1, wherein at least one of the plurality of point radiation sources includes at least one of:
   a high voltage generator configured to generate a high-voltage for a tube;
   the tube configured to generate the radiation beam based on the high-voltage;
   a filtering device configured to absorb a radiation beam lower than a preset energy range;
   a control device configured to control the high-voltage generated by the high voltage generator or the energy range of the radiation beam generated by the tube; or
   an electromagnetic coil configured to control a moving direction of the radiation beam.

10. The imaging system of claim 1, wherein each of the at least one radiation beam includes a plurality of X-ray photons, and the detector is further configured to:
    detect an energy of each of at least a portion of detected X-ray photons, and
    count the detected X-ray photons of different energy ranges.

11. The imaging system of claim 10, further comprising:
    a processing device configured to
    for each of the plurality of point radiation sources, determine a candidate image corresponding to the each point radiation source based on the energy range of the radiation beam emitted by the each point radiation source, energies of detected X-ray photons corresponding to the radiation beam, and the count of the detected X-ray photons corresponding to the radiation beam; and
    generate a target image based on the candidate images corresponding to the plurality of point radiation sources.

12. The imaging system of claim 1, wherein the subject is a breast, and the imaging system further comprises:
    a compression component located between the at least one array radiation source and the detector, the compression component being configured to position the breast, and
    the at least one array radiation source comprising:
    a linear array radiation source including a plurality of first point radiation sources, the linear array radiation source being configured on a chest-wall side of the breast, and
    a planar array radiation source including a plurality of second point radiation sources.

13. The imaging system of claim 12, wherein
the linear array radiation source forms a radiation region, and
a first radiation surface in the radiation region formed by the linear array radiation source is perpendicular to the compression component.

14. The imaging system of claim 13, further comprising:
a first shielding component configured to prevent a radiation beam emitted by the planar array radiation source from traversing the radiation region.

15. The imaging system of claim 14, wherein
the first shielding component is configured on the compression component, and
the first shielding component is parallel to a second radiation surface in the radiation region formed by the linear array radiation source, the first radiation surface being closer to the chest-wall side of the breast than the second radiation surface.

16. The imaging system of claim 12, further comprising:
a second shielding component configured to prevent a radiation beam emitted by the planar array radiation source or the linear array radiation source from traversing the chest-wall side of the breast.

17. The imaging system of claim 12, further comprising:
a third shielding component configured on at least one of a side perpendicular to the chest-wall side of the breast or a side opposite to the chest-wall side of the breast.

18. An imaging method implemented on a computing device having at least one processor and at least one storage device, the imaging method comprising:
providing a medical device including at least one array radiation source each of which includes a plurality of point radiation sources, the at least one array radiation source being configured to emit at least one radiation beam, and a detector configured to detect at least part of the at least one radiation beam, wherein the imaging device is a digital breast tomosynthesis (DBT) system;
obtaining, based on information of a subject to be scanned by the medical device, at least one parameter of the at least one array radiation source of the medical device;
causing the medical device to perform a scan on the subject based on the at least one parameter of the at least one array radiation source; and
generating an image of the subject based on the scan.

19. An imaging method implemented on a computing device having at least one processor and at least one storage device, the imaging method comprising:
causing each point radiation source of a plurality of point radiation sources of an array radiation source to simultaneously emit a radiation beam to a subject, each radiation beam including a plurality of X-ray photons, wherein the subject is located between the array radiation source and a detector, and at least two radiation beams emitted by the plurality of point radiation sources are different;
for each of the plurality of point radiation sources,
obtaining, by the detector, energies of detected X-ray photons corresponding to the radiation beam emitted by the each point radiation source and a count of the detected X-ray photons corresponding to the radiation beam; and
determining a candidate image corresponding to the each point radiation source based on an energy range of the radiation beam emitted by the each point radiation source, the energies of the detected X-ray photons corresponding to the radiation beam, and the count of detected X-ray photons corresponding to the radiation beam; and
generating a target image based on the candidate images corresponding to the plurality of point radiation sources.

20. The imaging system of claim 12, wherein an arrangement density of the plurality of first point radiation sources is higher than an arrangement density of the plurality of second point radiation sources.

* * * * *